(12) United States Patent
Katz

(10) Patent No.: US 8,263,141 B2
(45) Date of Patent: *Sep. 11, 2012

(54) TABLET WITH REMEDIAL COMPOSITION AND METHODS FOR TREATING MEDICAL DISORDERS AND AILMENTS

(75) Inventor: Daniel Katz, Misgav (IL)

(73) Assignee: Mediglobe Ltd., Ya'ad (IL)

( * ) Notice: Subject to any disclaimer, the term of this patent is extended or adjusted under 35 U.S.C. 154(b) by 154 days.

This patent is subject to a terminal disclaimer.

(21) Appl. No.: 12/789,764

(22) Filed: May 28, 2010

(65) Prior Publication Data

US 2010/0303904 A1     Dec. 2, 2010

Related U.S. Application Data

(63) Continuation-in-part of application No. 12/182,369, filed on Jul. 30, 2008, now Pat. No. 8,124,136.

(60) Provisional application No. 60/935,165, filed on Jul. 30, 2007.

(51) Int. Cl.
    *A01N 65/00*     (2009.01)

(52) U.S. Cl. ...................................................... 424/725

(58) Field of Classification Search ................. None
See application file for complete search history.

(56) References Cited

U.S. PATENT DOCUMENTS

| | | | |
|---|---|---|---|
| 5,401,504 A | 3/1995 | Das et al. |
| 5,494,668 A | 2/1996 | Patwardhan |
| 5,897,865 A | 4/1999 | Nguyen |
| 6,048,533 A | 4/2000 | Nguyen |
| 6,126,933 A | 10/2000 | Warne et al. |
| 6,159,983 A | 12/2000 | Bergeron, Jr. |
| 6,440,468 B1 | 8/2002 | Quintanilla Almagro et al. |
| 2006/0127505 A1 | 6/2006 | Haines et al. |
| 2006/0188471 A1 | 8/2006 | Podolsky et al. |
| 2009/0035371 A1 | 2/2009 | Katz |

OTHER PUBLICATIONS

Office Action issued Nov. 24, 2010 for U.S. Appl. No. 12/182,369, filed Jul. 30, 2008.
Response to Office Action filed Jun. 30, 2011 for Office Action issued Nov. 24, 2010 for U.S. Appl. No. 12/182,369, filed Jul. 30, 2008.
Restriction Requirement issued Apr. 5, 2010 for U.S. Appl. No. 12/182,369, filed Jul. 30, 2008.
Response to Restriction Requirement filed May 21, 2010 for Restriction Requirement issued Apr. 5. 2010 for U.S. Appl. No. 12/182,369, filed Jul. 30, 2008.
Office Action issued Aug. 3, 2010 for U.S. Appl. No. 12/182,369, filed Jul. 30, 2008.
Response to Office Action filed Sep. 17, 2010 for Office Action issued Aug. 3, 2010 for U.S. Appl. No. 12/182,369, filed Jul. 30, 2008.
Response to Office Action filed Feb. 21, 2011 for Office Action issued Nov. 24, 2010 for U.S. Appl. No. 12/182,369, filed Jul. 30, 2008.
Final Offce Action issued Apr. 21, 2011 for U.S. Appl. No. 12/182,369, filed Jul. 30, 2008.
Response to Final Office Action filed Jun. 30, 2011 for Final Office Action issued Apr. 21, 2011 for U.S. Appl. No. 12/182,369, filed Jul. 30, 2008.

*Primary Examiner* — Michael Meller
(74) *Attorney, Agent, or Firm* — Martin Fleit; Paul D. Bianco; Fleit Gibbons Gutman Bongini & Bianco PL

(57) ABSTRACT

The invention discloses a pharmaceutical composition useful for treatment and prevention of medical disorders and ailments. The aforesaid composition comprises active ingredients comprising; Turmeric extract, Turmeric powder, Selenium or source of Selenium, especially Selenomethionine, and Green tea extract. The disclosed pharmaceutical composition is especially adapted for treatment of inflammatory bowel disease (IBD) and colorectal cancer (CRC).

8 Claims, 18 Drawing Sheets

Normal mucosa  Small ACF  Large ACF

TABLET WITH REMEDIAL COMPOSITION AND METHODS FOR TREATING MEDICAL DISORDERS AND AILMENTS

FIELD OF THE INVENTION

The present invention relates to a pharmaceutical composition, effective for the treatment and the prevention of medical disorders and ailments, especially inflammatory bowel disease and colorectal cancer. The invention also pertains to a method for treating and preventing medical disorders and ailments, especially inflammatory bowel disease and colorectal cancer, comprising obtaining a pharmaceutical composition as defined above.

This application claims priority of U.S. patent application Ser. No. 12/182,369 filed Jul. 30, 2008.

BACKGROUND OF THE INVENTION

*Curcuma longa* (Fam. Zingiberaccae) or Turmeric is one of the oldest herbs in Ayurveda materia medica, and has been used in Ayurveda medicine internally as a stomach, tonic and blood purifier, and topically in the prevention and treatment of skin diseases. The significance of turmeric in medicine has changed considerably since the very recent discovery of the anti-oxidant properties of naturally occurring phenolic compounds. The same ground dried rhizome of *Curcuma longa*, which has been used for centuries as a spice, food preservative and a coloring agent, has been found to be a rich source of phenolic compounds or curcuminoids.

At the present time Turmeric is used for healing wounds, skin disorders, as a component of immunomodulators, see or example U.S. Pat. Nos. 5,401,504, 5,494,668, 5,897,865 and 6,048,533.

Colorectal Cancer (CRC) is one of the leading causes of cancer death in the Western world. Patients with Inflammatory Bowel Disease (IBD) are at a substantially increased risk for development of Colorectal Cancer (CRC) compared with the general population. Although IBD contributes only a small proportion (less than 1%) of all new cases of CRC, 15% of all deaths in IBD patients are due to CRC, and because there is still no ideal treatment for CRC and the 5-year survival rate is low (<50%), chemoprevention has become an increasingly important consideration in IBD.

Several studies indicate that COX-2 inhibitors may prevent CRC. However, their long-term use is limited due to gastrointestinal (GI) and cardiovascular side effects. 5-aminosalicylic acid (5-ASA) (mesalamine) is an anti-inflammatory drug, see e.g., U.S. Pat. No. 6,159,983; that has been extensively used in the treatment of IBD. It is well tolerated by most patients, and has limited systemic adverse effects and gastrointestinal toxicity. As chemoprevention of CRC must meet very high standards of safety and efficacy, 5-ASA has a well-established place in the management of patients suffering from IBD. Although 5-ASA is considered to be a safe drug in treatment of IBD and its adverse effects are relatively few, early reports suggest that the potential toxicity of 5-ASA should be considered, in particular during long-term treatment with 5-ASA. One of the lessons learned from cancer research in recent years is that combinatorial strategies in cancer therapy can provide dramatic improvement in safety and efficacy over monotherapy regimens, especially if the drugs differ in their mode of action. Furthermore, reduced toxicity can be achieved particularly when the combination is comprised of a commonly used dietary factor or natural herb.

There is an unmet need therefore to provide a composition useful in a therapy for IBD and CRC, which overcomes the above deficiencies, using a combination of natural ingredients.

SUMMARY OF THE INVENTION

It is hence one object of the invention to disclose a pharmaceutical composition consisting of natural ingredients, said pharmaceutical composition is useful for treatment and prevention of medical disorders and ailments, said medical disorders and ailments are selected from a group consisting of inflammatory bowel disease (IBD) and colorectal cancer (CRC). The aforesaid composition comprises: (a) a turmeric based first active ingredient, comprising; Turmeric extract and Turmeric powder; and (b) a second non turmeric based active ingredient, wherein said second active ingredient comprises a selenium element selected from a group consisting of Selenium, source of Selenium, and Selenomethionine and a Green tea extract. Another object of the invention is to disclose the aforesaid pharmaceutical composition, wherein the Turmeric extract is provided in about 200 to about 300 mg, the Turmeric extract comprises about 95% curcuminoids; Turmeric powder is provided in about 200 to about 300 mg; Green tea extract is provided in about 200 to about 300 mg, the Green tea comprises about 50% to about 70% polyphenols; and selenium element provided in about 80 to about 120 μg of Selenium (elemental).

It is a further object of the invention to disclose the aforesaid pharmaceutical composition wherein the composition is formulated in a form selected from a group consisting of a tablet, caplet, capsule, lozenge, dragee and sachet form.

It is a further object of the invention to disclose the aforesaid pharmaceutical composition further comprising enteric coating encapsulating the same, wherein the enteric coating imparts protection to the composition so that the composition is protected in a low pH environment of about 3 or less while capable of releasing the composition at a pH of about 5.5 or higher.

It is a further object of the invention to disclose the aforesaid pharmaceutical composition wherein the composition is coated by the enteric coating Eudragit™.

It is still a further object of the invention to disclose the aforesaid pharmaceutical composition additionally comprising 5-ASA (mesalamine).

It is still a further object of the invention to disclose the aforesaid pharmaceutical composition, wherein the pharmaceutical composition confers a synergistic therapeutic effect on subjects with respect to treatment of said IBD and/or CRC.

It is still a further object of the invention to disclose the aforesaid pharmaceutical composition wherein the composition confers therapeutic effect on subjects with respect to development of IBD and/or CRC parameters.

It is still a further object of the invention to disclose the aforesaid pharmaceutical composition wherein the composition confers therapeutic effect on subjects with respect to development of IBD and/or CRC parameters as compared to untreated controls, said parameters are selected from a group consisting of Disease Activity Index (DAI), induction and severity of colitis, macro-histological score damage, Aberrant Crypt Foci (ACF) formation, number of crypts and level of C-reactive protein (CRP).

It is still a further object of the invention to disclose the aforesaid pharmaceutical composition wherein the composition provides a decrease in at least one of IBD or CRC parameters of at least 30%, the parameters selected from a group consisting of Disease Activity Index (DAI), induction and severity of colitis, macro-histological score damage, number of crypts, level of C-reactive protein (CRP) compared to untreated controls.

It is still a further object of the invention to disclose the aforesaid pharmaceutical composition wherein the composition confers a synergistic therapeutic effect on subjects with respect to development of IBD and/or CRC parameters compared to the therapeutic effect on said subject when said active ingredients of said pharmaceutical composition are administered to said subject separately and or in partial combination.

It is still a further object of the invention to disclose the synergistic effect as defined above adapted to be at least 15% higher relative to the therapeutic effect on subjects with respect to development of IBD and/or CRC parameters when active ingredients of the pharmaceutical composition are administered to the subject separately and or in partial combination.

It is still a further object of the invention to disclose the aforesaid pharmaceutical composition wherein the pharmaceutical composition provides a decrease in DAI score greater than the decrease provided by administering the active ingredients of the pharmaceutical composition to the subject separately or in partial combination.

It is still a further object of the invention to disclose the aforesaid pharmaceutical composition wherein the pharmaceutical composition provides a decrease in induction and severity of colitis greater than the decrease provided by administering the active ingredients of the pharmaceutical composition to the subject separately or in partial combination.

It is still a further object of the invention to disclose the aforesaid pharmaceutical composition, wherein the pharmaceutical composition provides a decrease in number of Crypts and/or ACF formation greater than the decrease provided by administering the active ingredients of the pharmaceutical composition to the subject separately or in partial combination.

It is still a further object of the invention to disclose the aforesaid pharmaceutical composition, wherein the pharmaceutical composition provides a decrease in the level of C-reactive protein (CRP) greater than the decrease provided by administering the active ingredients of the pharmaceutical composition to the subject separately or in partial combination.

It is still a further object of the invention to disclose a method for treating and preventing medical disorders and ailments, especially inflammatory bowel disease and colorectal cancer, comprising; obtaining a pharmaceutical composition consisting of natural ingredients comprising; a turmeric based first active ingredient comprising, Turmeric extract; and Turmeric powder; and a second non turmeric based active ingredient, comprising Green tea extract; and, a Selenium element selected from a group consisting of Selenium, source of Selenium and Selenomethionine. The method further comprises administering the pharmaceutical composition to a patient according to a predetermined protocol.

It is still a further object of the invention to disclose the method as defined above, wherein the Turmeric extract is provided in bout 200 to about 300 mg, about 95% curcuminoids; the Turmeric powder is provided in about 200 to about 300 mg; the Green tea extract is provided in about 200 to about 300 mg, about 50% to about 70% polyphenols and the Selenium element is provided with about 80 to about 120 ng Selenium.

It is still a further object of the invention to disclose a method for treating and preventing medical disorders and ailments, especially inflammatory bowel disease and colorectal cancer. The aforesaid method comprises steps of obtaining the pharmaceutical composition comprising the following active ingredients: (i) Turmeric extract, containing about 200 to about 300 mg, about 95% curcuminoids; (ii) Turmeric powder, containing about 200 to about 300 mg; (iii) Green tea extract, containing about 200 to about 300 mg, about 50% to about 70% polyphenols and; (iv) Selenomethionine, containing about 80 to about 120 ng Selenium. The aforesaid method further comprises the following steps: coating the pharmaceutical composition with enteric coating encapsulating the same and, administering the pharmaceutical composition to a patient according to a predetermined protocol.

It is still a further object of the invention to disclose the method as defined above wherein the method further comprises steps of formulating said composition in a form selected from a group consisting of tablet, caplet, capsule, lozenge, dragee or sachet form.

It is still a further object of the invention to disclose the method as defined above wherein the method further comprises steps of coating said pharmaceutical composition with enteric coating the enteric coating especially relates to the enteric coating component Eudragit™.

It is still a further object of the invention to disclose the method as defined above wherein the method further comprises steps of providing protection to said composition so that said composition is protected in a low pH environment of about 3 or less while capable of releasing said composition at a pH of about 5.5 or higher.

It is still a further object of the invention to disclose the method as defined above wherein the method, additionally comprises steps of administering said pharmaceutical composition as a combined treatment with Mesalamine (5-ASA) before, whilst or after the step of abating the pharmaceutical composition.

It is still a further object of the invention to disclose the method as defined above wherein the method additionally comprises steps of administering said pharmaceutical composition as a combined treatment with 5-ASA such that said treatment confers a synergistic therapeutic effect on subjects with respect to treatment of said IBD and/or CRC.

It is still a further object of the invention to disclose the method as defined above wherein the method further comprises steps of conferring therapeutic effect on subjects with respect to development of IBD and/or CRC parameters compared to untreated controls, said parameters selected from a group consisting of DAI, induction and severity of colitis, macro-histological score damage, ACF formation, number of crypts, level of C-reactive protein (CRP).

It is still a further object of the invention to disclose the method as defined above wherein the method further comprises steps of providing a decrease in at least one of IBD or CRC parameters of at least 30%, said parameters selected from a group consisting of DAI, induction and severity of colitis, macro-histological score damage, number of crypts, level of C-reactive protein (CRP) compared to untreated controls.

It is still a further object of the invention to disclose the method as defined above wherein the method additionally comprises steps of combining the ingredients in predetermined amounts and proportions sufficient to confer a synergistic therapeutic effect on subjects with respect to development of IBD and/or CRC parameters and administering same.

It is still a further object of the invention to disclose the method as defined above wherein the method further comprises steps of combining said active ingredients in predetermined amounts and proportions sufficient to confer a synergistic effect adapted to provide at least 15% increase relative to the therapeutic effect on subjects with respect to development of IBD and/or CRC parameters when active ingredients of the pharmaceutical composition are administered to the subject separately and or in partial combination. It is still a further object of the invention to disclose the method as defined above additionally comprises steps of administering said pharmaceutical composition to said patient such that the decrease in DAI score is greater than the decrease provided by administering the active ingredients of the pharmaceutical composition to the subject separately or in partial combination.

It is still a further object of the invention to disclose the method as defined above wherein the method additionally comprises steps of administering said pharmaceutical composition to said subject such that the decrease in induction and severity of colitis is greater than the decrease provided by administering the active ingredients of the pharmaceutical composition to the subject separately or in partial combination.

It is still a further object of the invention to disclose the method as defined above wherein the method additionally comprises steps of administering said pharmaceutical composition to said subject such that the decrease in number of Crypts and/or ACF formation is greater than the decrease provided by administering the active ingredients of the pharmaceutical composition to the subject separately or in partial combination.

It is still a further object of the invention to disclose the method as defined above wherein the method additionally comprises steps of administering said pharmaceutical composition to said subject such that the decrease in the level of C-reactive protein (CRP) is greater than the decrease provided by administering the active ingredients of the pharmaceutical composition to the subject separately or in partial combination.

It is still a further object of the invention to disclose the method as defined above useful for treating Inflammatory Bowel Disease (IBD) and Colorectal Cancer (CRC).

BRIEF DESCRIPTION OF THE FIGURES

In order to understand the invention and to see how it may be implemented in practice, a plurality of embodiments is adapted to now be described, by way of non-limiting example only, with reference to the accompanying drawings; wherein.

DETAILED DESCRIPTION OF THE INVENTION

Figure 1:
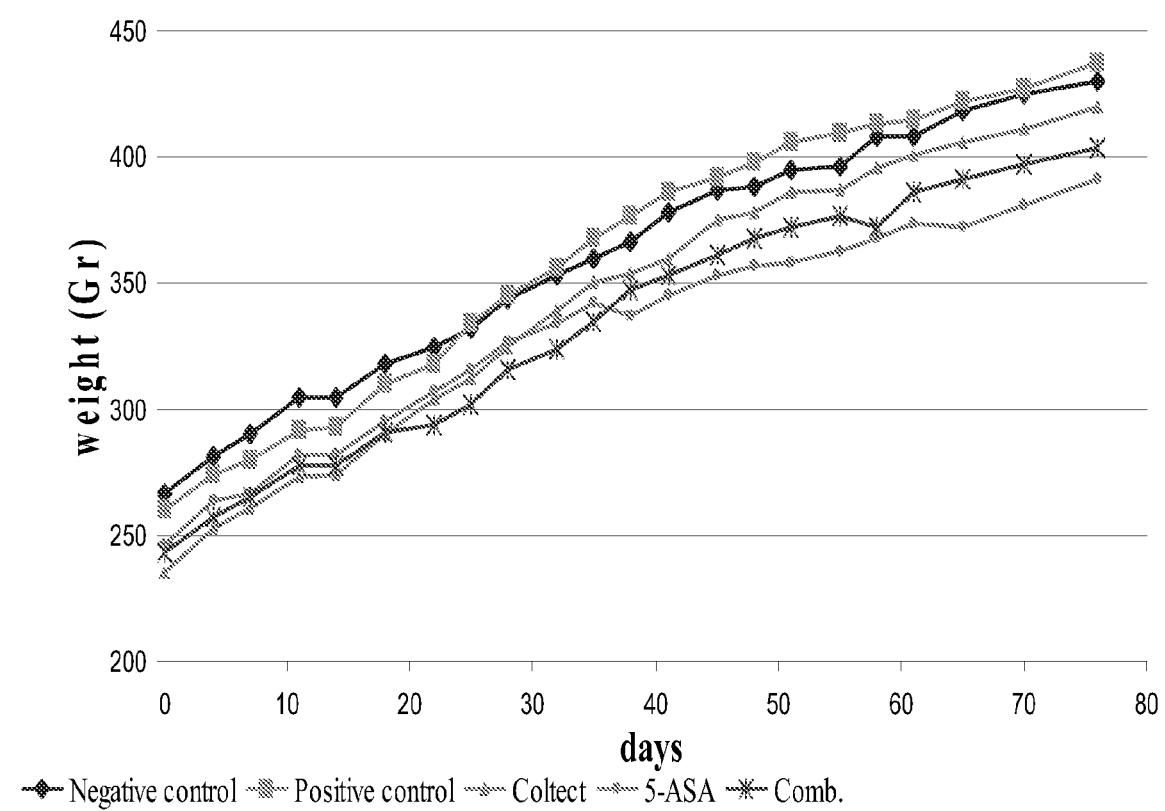
FIG. 1 is a graphical representation of the changes in body weight of DMH-induced model rats.

The following description is provided, alongside all chapters of the present invention, so as to enable any person skilled in the art to make use of said invention and sets forth the best modes contemplated by the inventor of carrying out this invention. Various modifications, however, is adapted to remain apparent to those skilled in the art, since the generic principles of the present invention have been defined specifically to provide a pharmaceutical composition with remedial composition and methods for treatment of medical disorders and ailments.

The present invention provides a pharmaceutical composition consisting of natural ingredients. The composition is useful for treatment and prevention of medical disorders and ailments, selected from a group consisting of inflammatory bowel disease (IBD) and colorectal cancer (CRC). The aforementioned composition comprising;
a. a turmeric based first active ingredient. The active ingredient further comprising;
   i. Turmeric extract; and,
   ii. Turmeric powder; and,
b. a second non turmeric based active ingredient, wherein said second active ingredient comprises a selenium element selected from a group consisting of Selenium, source of Selenium, and Selenomethionine; and, a Green tea extract.

In accordance with the current invention a remedial composition used in the form of tablet, caplet, capsule, lozenge, dragee or sachet coated by enteric coating and comprising about 250 mg of turmeric extract, about 250 mg of turmeric powder, about 250 mg of green tea extract, and about 100 µg of Selenomethionine is offered for healing and prevention of IBD and CRC.

The term 'about' refers hereinafter to a measure being plus or minus 10% of the defined measure.

The term 'IBD' refers hereinafter to the major types of IBD which include Crohn's disease and ulcerative colitis.

The term 'CRC' refers hereinafter to colorectal cancer, also called colon cancer or large bowel cancer, which includes cancerous growths in the colon, rectum and appendix.

The remedial composition has an anti-inflammatory effect and can be used to prevent and treat ulcerative colitis and Crohn's disease. Additionally, the remedial composition can be used as a drug enabling to decrease incidence of CRC.

IBD was suggested as a factor involved in increased propensity for development of CRC. Hence IBD prevention may decreases incidence of CRC. One approach for treating CRC is by using COX-2 inhibitors. Previous studies have shown that curcumin potentiates the growth inhibitory effect of Celecoxib, a specific COX-2 inhibitor.

The remedial composition of the present invention can be used in a drug regime for preventing or at least lowering the incidence of CRC. The main advantage of the remedial composition is low toxicity. There is, up to now, no evidence of substantial side effects through the use of the invented pharmaceutical composition in long-term preventive treatment. The remedial composition treatment can be combined with 5-ASA (mesalamine) The aforementioned combination of the remedial composition and 5-ASA (mesalamine) gave good results. This is especially important since combinatorial strategies in cancer therapy can provide dramatic improvement in safety and efficacy over monotherapy regimens, especially if the drugs differ in their mode of action. Mesalazine (INN, BAN), also known as Mesalamine (USAN) or 5-aminosalicylic acid (5-ASA), is an anti-inflammatory drug used to treat inflammation of the digestive tract (Crohn's disease) and mild to moderate ulcerative colitis. Mesalazine is a bowel-specific aminosalicylate drug that is metabolized in the gut and has its predominant actions there, thereby having fewer systemic side effects. As a derivative of salicylic acid, 5-ASA is also an antioxidant that traps free radicals, which are potentially damaging by-products of metabolism. 5-ASA is considered the active moiety of Sulfasalazine which is its metabolic precursor.

Turmeric (*Curcuma longa*) is a rhizomatous herbaceous perennial plant of the ginger family, Zingiberaceae which is native to tropical South Asia. It needs temperatures between 20 and 30 deg. C. and a considerable amount of annual rainfall to thrive. Plants are gathered annually for their rhizomes, and re-seeded from some of those rhizomes in the following season. The term 'Turmeric extract' refers hereinafter in a non-limiting manner to a bright yellow/orange polyphenol, particularly to extracts of *Curcuma Longa* Linn.; and especially to 1,7-Bis(4-hydroxy-3-methoxyphenyl)-1,6-heptadiene-3,5-dione and derivatives thereof. Turmeric powder is a powder of Turmeric as defined above.

The health benefits of tea have been touted for infusions made from the plant *Camellia sinensis* for over 4700 years; ever since its discovery was attributed to the legendary emperor, Shennong. The Shen Nong Ben Cao Jing claimed its taste and stimulative properties were useful for treating tumors, abscesses, bladder ailments, lethargy, among other conditions. The possible beneficial health effects of tea consumption have been suggested and supported by some studies, but others have found no beneficial effects. The studies contrast other claims, including antinutritional effects such as preventing absorption of iron and protein, usually attributed to tannin. The vast majority of studies have been of Green tea; however some studies have been made of the other types of tea derived from *Camellia sinensis* such as White tea, Oolong tea, and Black tea. Green tea has been claimed to be helpful for atherosclerosis, LDL cholesterol, cancer, inflammatory bowel disease, diabetes, liver disease, weight loss, cognitive impairment, and even halitosis.

The term 'Green tea extract' refers hereinafter in a non-limiting manner to product derived from the leaves of the *Camellia sinensis* plant. The term also relates to plant extracts or products thereof comprising polyphenols which are classified as catechins. Green tea contains six primary catechin compounds: catechin, gallaogatechin, epicatechin, epigallocatechin, epicatechin gallate, and apigallocatechin gallate (also known as EGCG or catechin). The term also refers to plant-originated products comprising alkaloids including caffeine, theobromine, and theophylline. These alkaloids provide green tea's stimulant effects.

The term 'Catechins' and 'epicatechin' are interchangeably refer hereinafter to one or more polyphenolic antioxidant plant metabolites, specifically flavonoids called flavan-3-ols. Although present in numerous plant species, the largest source in the human diet is from various teas derived from the tea-plant *Camellia sinensis*. Catechin and epicatechin are epimers, with (−)-epicatechin and (+)-catechin being the most common optical isomers found in nature. Catechin was first isolated from the plant extract catechu, from which it derives its name. Heating catechin past its point of decomposition releases pyrocatechol, which explains the common origin of the names of these compounds. Epigallocatechin and gallocatechin contain an additional phenolic hydroxyl group when compared to epicatechin and catechin, respectively, similar to the difference in pyrogallol compared to pyrocatechol.

The term 'selenium element' or 'Selenomethionine' refers hereinafter interchangeably to selenium, to any source of selenium, and especially (yet not exclusively) to Selenomethionine an amino acid containing selenium. The L-isomer of selenomethionine, known as Se-met, is a common natural food source of selenium. It can not be synthesized by higher animals, but can be obtained from plant material. Incorporation of Selenomethionine into proteins in place of Methionine aids the structure elucidation of proteins by X-ray crystallography using multi-wavelength anomalous diffraction (MAD). The incorporation of heavy atoms such as Selenium helps solving the phase problem in X-ray crystallography.

An enteric coating is a barrier applied to oral medication that controls the location in the digestive system where it is absorbed. Enteric refers to the small intestine; therefore enteric coatings prevent release of medication before it reaches the small intestine. Most enteric coatings work by presenting a surface that is stable at the highly acidic pH found in the stomach, but breaks down rapidly at a less acidic (relatively more basic) pH. For example, they will not dissolve in the acidic juices of the stomach (pH ~3), but they will in the higher pH (above pH 5.5) environment present in the small intestine. The term 'enteric coating' refers hereinafter to encapsulating means, coated with a material that permits transit through the stomach to the small intestine before the medication is released.

The term 'about pH' refers hereinafter to a measure being plus or minus 1 unit of the defined measure of pH.

The term 'parameters' refers hereinafter to Disease Activity Index (DAI) score, macroscopic injury evaluation, macrohistological score damage, induction and severity of colitis, Aberrant Crypt Foci (ACF) formation, number of crypts and levels of C-Reactive Protein (CRP).

The term 'active ingredients' refers hereinafter to Turmeric extract, Turmeric powder, Curcumin, Selenium, Selenomethionine, Green tea extract, polyphenols.

The term 'therapeutic effect' refers hereinafter to the improvement in IBD and/or CRC parameters. The therapeutic effect further includes the chemopreventive effect.

The therapeutic effects of the disclosed pharmaceutical composition in treating inflammatory bowel disease and colorectal cancer in model animals is hereby presented:

EXAMPLES

A pharmaceutical composition was made, comprising Turmeric extract (95% curcuminoids), 250 mg; Turmeric powder, 250 mg; Green tea extract (60% polyphenols, 25% epigallocatechin gallate EGCG), 250 mg; Selenium (as Selenomethionine), 100 µg; Enteric coating, here, commercially available Eudragit™ both inflammatory bowel disease and colorectal cancer was relieved.

Example 1

Evaluation of Chemopreventive Effects of Coltect (Curcumin-Selenium-Green Tea Mixture), 5-ASA and their Combination in the 1,2-Dimethylhydrazine (DMH)-Induced CRC Model of Aberrant Crypt Foci (ACF) in Rats ACF Induction and Experimental Design Age- and sex-matched 23 Wistar rats were purchased from the animal facilities at the Tel-Aviv Sourasky Medical Center (TASMC). The rats were injected subcutaneously twice a week for two weeks with 0.3 ml of 30 mg/kg body weight DMH (Sigma-Aldrich, Israel) dissolved in PBS, and groups (n=5) were randomly divided as follows (Table 1):
1. Negative control-rats injected subcutaneously with PBS.
2. Positive control-non-treated rats, injected subcutaneously with DMH.
3. Rats treated with Coltect (150 mg/kg body weight).
4. Rats treated with 5-ASA (50 mg/kg body weight).
5. Rats treated with 5-ASA (50 mg/kg body weight) and Coltect (30 mg/kg body weight).

TABLE 1

DMH induced rat groups

| Group | No. of rats | DMH | Treatment |
|---|---|---|---|
| 1 | 3 | 0 | — |
| 2 | 5 | 30 mg/kg | — |
| 3 | 5 | 30 mg/kg | Coltect |
| 4 | 5 | 30 mg/kg | 5-ASA |
| 5 | 5 | 30 mg/kg | 5-ASA + Coltect |

Rats injected subcutaneously with PBS served as the negative control group (n=3).

The Coltect mixture was dissolved in a solution of DMSO (50%) and tap water. The solution was administered to the rats by oral gavage for five days, starting at the first day of DMH injections. During the experiment, the rats were weighed twice a week.

ACF Staining

Sixty days after DMH injections the rats were sacrificed by $CO_2$ flow. The colons were removed and flushed with isotonic saline solution, opened longitudinally, cut into three parts of equal length, and labeled as proximal, middle and distal segments. The colons were laid open on a Wattman paper and fixed flat in 4% buffered formalin solution. The ACF were visualized and counted by using methylene blue staining (0.2% solution) and photographed. Briefly, the colons were immersed in the methylene blue solution for 5 minutes, washed with saline, placed on a petri dish and transilluminated under a dissecting microscope (×40). The number and multiplicity of ACF for each colonic segment were evaluated and recorded. The number and multiplicity of ACF were recorded separately for each segment. To determine multiplicity of ACF, the number of crypts in each focus was defined and recorded.

Results

Figure 2A:
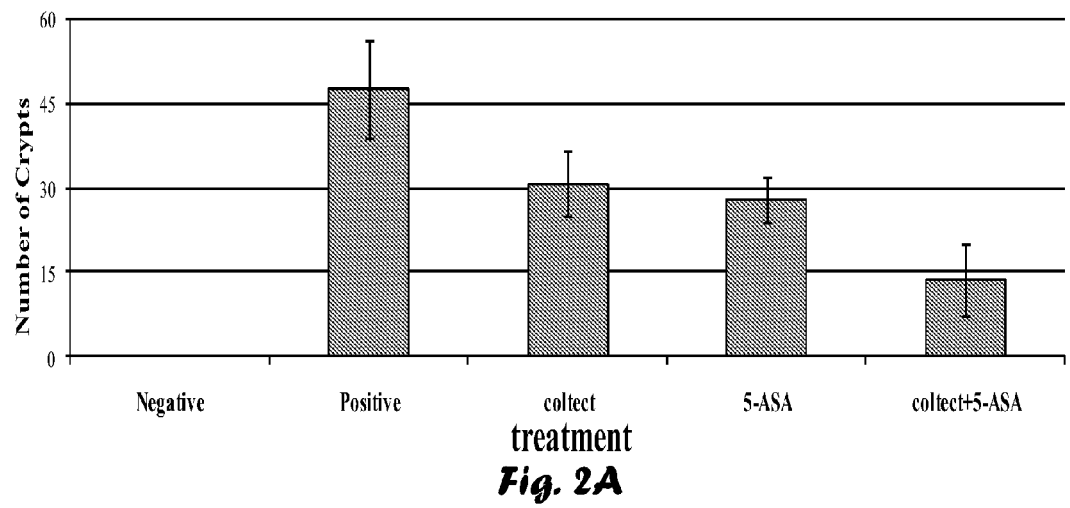
FIG. 2A is a graphical representation of the number of crypts (1-3) in treated colons.
Figure 2B:
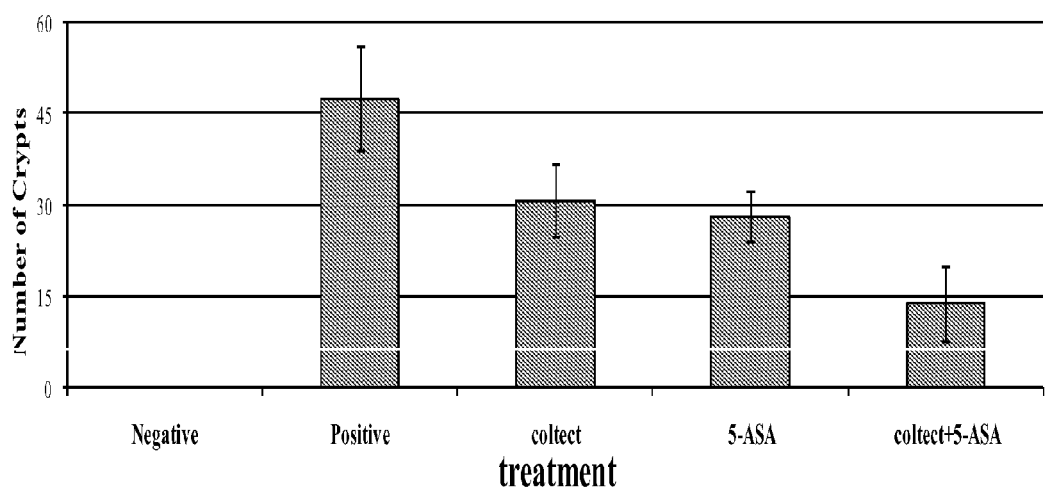
FIG. 2B is a graphical representation of the number of crypts (>4) in treated colons.
Figure 3:
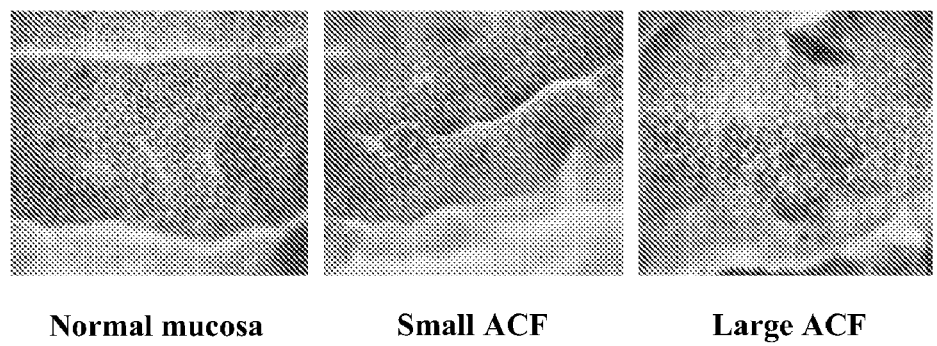
FIG. 3 is a photographic visualization of ACFs in colon sections stained with Methylene blue.

During the experiment the rats did not exhibit any radical changes in their weight (FIG. 1). Table 2 and FIGS. 2 and 3 show the number of ACFs in colons treated with Coltect, 5-ASA and their combination as compared to the positive control.

TABLE 2

Number of crypts in treated colons

| Group | 1-3 crypts | >4 crypts |
|---|---|---|
| Negative control | 0 | 0 |
| Positive control | 47.5 ± 8.7 | 19 ± 5.3 |
| Coltect | 31 ± 5.9 | 12 ± 5.4 |
| 5-ASA | 28 ± 4.1 | 11.6 ± 3.9 |
| Coltect + 5-ASA | 14 ± 6.3 | 6 ± 1.1 |

Table 2 and FIGS. 2 and 3 relate to DMH-induced model rats. The number of ACF in the Coltect treated rats was reduced by an average of about 40% as compared to the positive control. However, treating the DMH-induced rats with a combination of the Coltect mixture and 5-ASA drug caused a reduction of an average of about 70% in the number of crypts as compared to the positive control.

Thus, these results demonstrate the effectiveness of the Coltect mixture in treating ACF in model rats. Moreover these experiments show the substantial improvement provided by administering combined therapy comprised of natural ingredients, namely the Coltect mixture of the present invention, and 5-ASA as a chemopreventive drug for treatment of colorectal cancer.

Example 2

Effects of 5-ASA, Coltect and their Combination in Dextran Sodium Sulphate (DSS)-Induced IBD Model in Mice Age- and sex-matched C57BL 5-weeks old female mice were obtained from Harlan Laboratories, Israel. After one week of acclimatization, the mice (n=36) were treated with 2.5% DSS (MP Biomedicals, LLC, France) administered in the drinking water for 5 days ad libitum, followed by two days of tap water. Four mice received saline (2.5%) and served as the negative control group. The mice were randomly divided into groups (n=8) and received the corresponding treatment starting from the first day for 7 days (Table 3). The treatments were given in doses of 0.5 ml of tap water with 2% DMSO by oral gavage. The following doses were used: Coltect—150 mg/kg body weight; 5-ASA—50 mg/kg body weight.

TABLE 3

DSS induced mice groups

| Group | No. of mice | DSS | Treatment |
|---|---|---|---|
| 1 | 4 | 0 | — |
| 2 | 8 | 2.5% | — |
| 3 | 8 | 2.5% | Coltect |
| 4 | 8 | 2.5% | 5-ASA |
| 5 | 8 | 2.5% | 5-ASA + Coltect |

All mice were sacrificed 7 days after the enema, their spleen and colon were removed, fixed in 10% formalin for histological evaluation and parts were frozen at 80° C. for later examination.

Macroscopic and Histological Evaluation:

For macroscopic injury evaluation a revised colonic damage scoring system was used as described by Morris et al. Thus, the severity of colitis was determined based on the following parameters:
1. Disease Activity Index (DAI): weight loss, gross bleeding, stool consistency (Table 2)—were daily recorded.
2. Spleen weight.
3. Colon length.
4. Histological score.

For histological injury evaluation tissues fixed in 10% formalin, were embedded in paraffin wax and cut. 4 μm sections were histologically stained and evaluated by light microscopy for ulceration and inflammation.

TABLE 4

DAI Score

| | Weight loss (%) | Gross bleeding | Stool consistency |
|---|---|---|---|
| 0 | <1% | Normal | Normal |
| 1 | 1-5% | | |
| 2 | 6-10% | Minor | |
| 3 | 11-15% | | |
| 4 | >15% | Gross bleeding | Diarrhea |

Two separate experiments were conducted. The results are shown separately for each experiment: FIG. 4 show the results of the first experiment. The results of the second experiment are shown in FIG. 5.

Figure 4A:
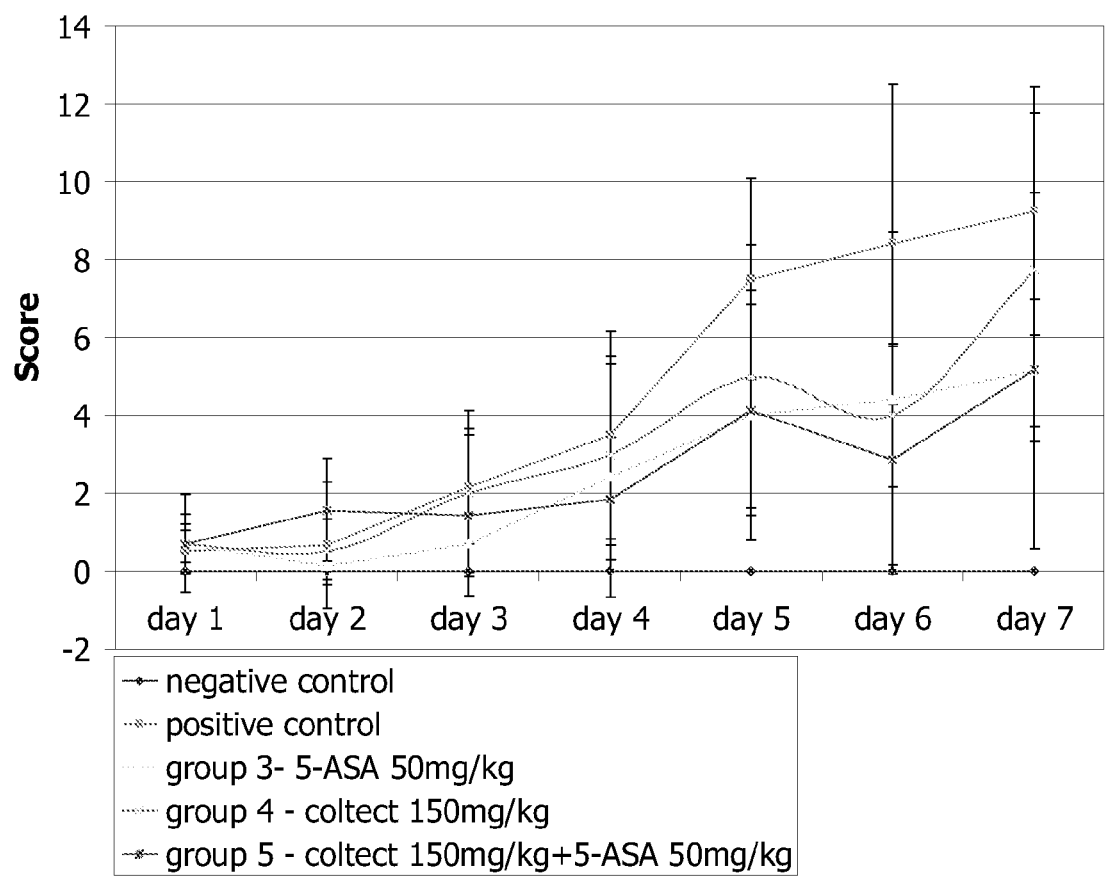
FIG. 4A is a graphical representation of the DAI score of the first experimental group of DSS-induced model mice.

Reference is now made to FIG. 4A which relates to the DAI score in DSS-induced IBD model mice. A significant reduction in DAI score was observed in mice treated with the combination of Coltect mixture of the present invention and 5-ASA. This is in comparison to DSS-induced mice, treated with 5-ASA or Coltect separately, which showed relatively higher DAI scores and therefore lower effect of the treatment.

Figure 4B:
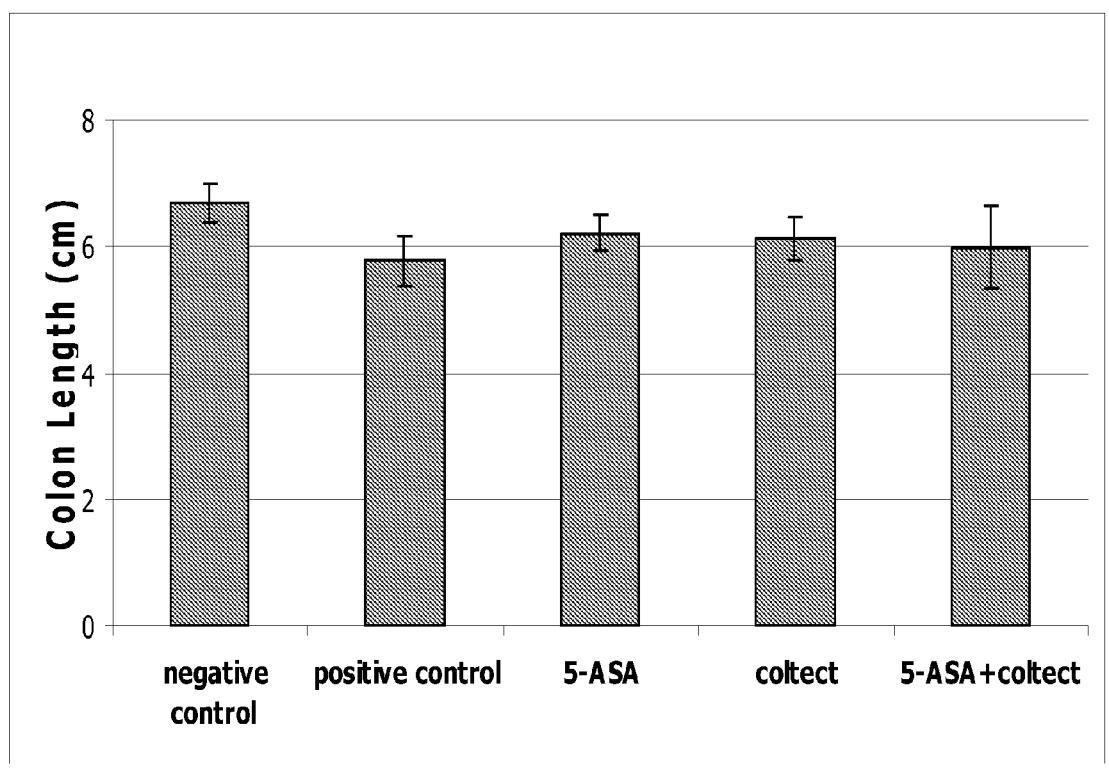
FIG. 4B is a graphical representation of the colon length of the first experimental group of DSS-induced model mice.

Reference is now made to FIG. 4B showing the colon length of the DSS-induced treated mice. No significant changes in colon length were observed with respect to the different treatments in the DSS-induced mice. Nevertheless, it is envisaged that an improvement in these results can be achieved without undue experimentation.

Figure 5A:
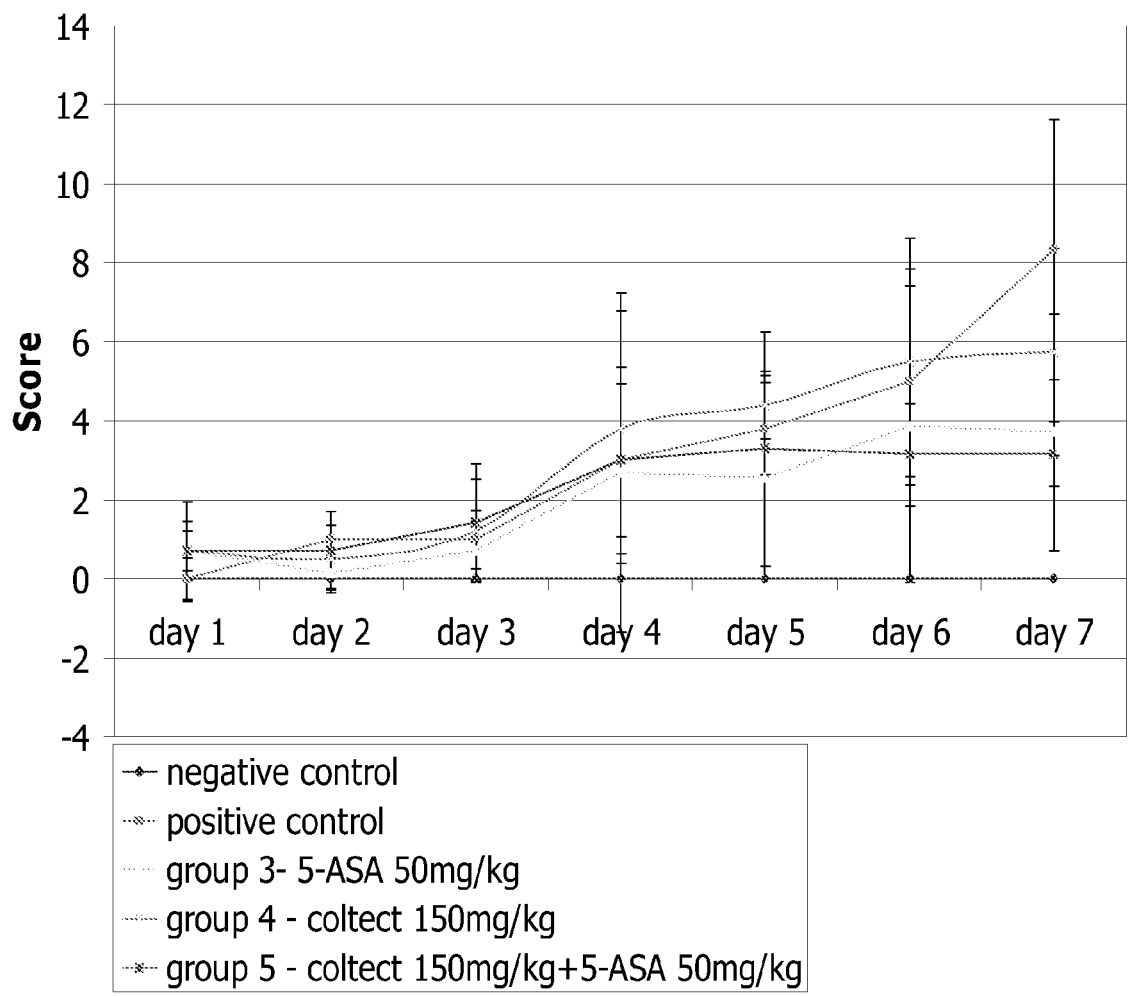
FIG. 5A is a graphical representation of the DAI score of the second experimental group of DSS-induced model mice.

Reference is now made to FIG. 5 which describes the results of the second experiment in DSS-induced IBD treated mice. FIG. 5A relates to the DAI score in the aforementioned mice treated with Coltect mixture, 5-ASA drug or with their combination. The mice treated with the Coltect mixture showed a reduction in DAI score at day 7 of the treatment as compared to the positive control. However the most significant reduction in DAI score was exhibited as a result of treating the mice with the combination of the Coltect mixture and 5-ASA drug. These results indicate the effectiveness of treating DSS-induced IBD mice with the Coltect mixture and 5-ASA combination.

Figure 5B:
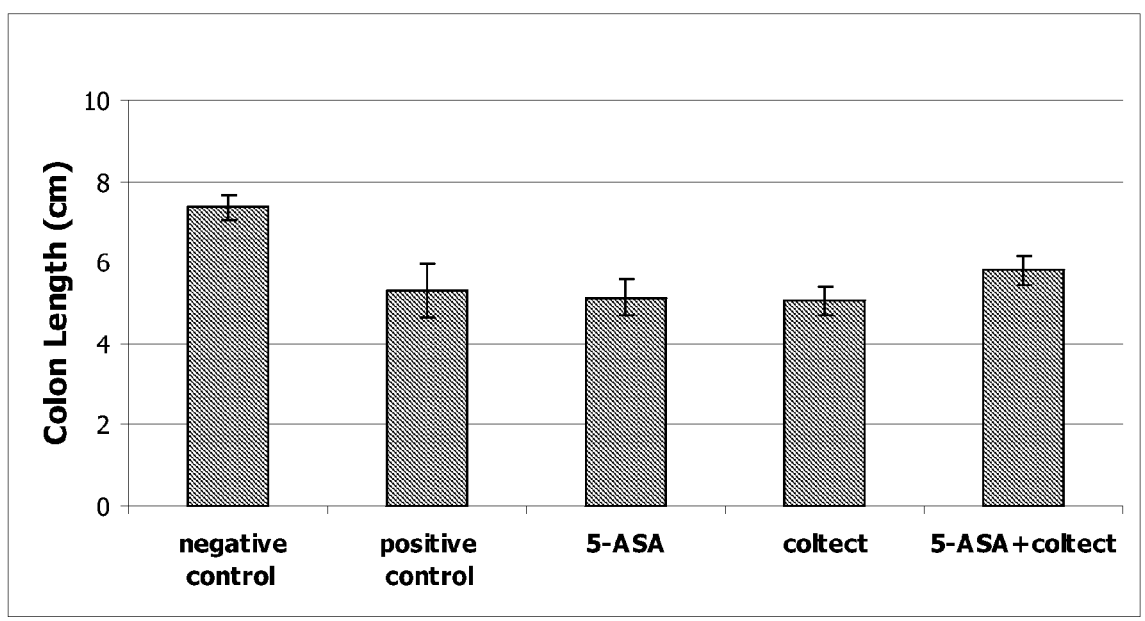
FIG. 5B is a graphical representation of the colon length score of the second experimental group of DSS-induced model mice.

FIG. 5B demonstrates that by treating DSS-induced mice with the combination of the 5-ASA drug and the Coltect mixture, a relative recovery in the colon length was detected. This is in comparison to the positive control and to the application of each treatment separately.

Combining the results described in the above experiments, it can be concluded that treating DSS-induced IBD model mice with Coltect mixture of the present invention effectively reduced the severity of IBD symptoms with respect to the number of crypts, DAI score and colon length. The effect of the Coltect mixture on curing DSS-induced IBD mice was significantly raised by the combined administration of the Coltect mixture and the 5-ASA drug.

Example 3

Effects of 5-ASA, Coltect and their Combination in 2,4,6-Trinitrobenzenesulfonic Acid (TNBS)-Induced IBD Model in Rats Twenty three female Wistar rats, 6-8-weeks old, were randomly divided into 5 treatment groups as shown in Table 5.

TABLE 5

TNBS induced mice groups

| Group | No. of rats | TNBS | Treatment |
|---|---|---|---|
| 1 | 3 | — | — |
| 2 | 5 | 10 mg | — |
| 3 | 5 | 10 mg | Coltect (150 mg/kg) |
| 4 | 5 | 10 mg | 5-ASA (50 mg/kg) |
| 5 | 5 | 10 mg | Coltect + 5-ASA |

One day before the experiment the rats were weighted, marked according to the groups, and fasted for 24 hours (for colon emptying). At the day of the experiment the rats were anesthetized by an intra-peritoneal injection of halothene and colitis was induced by intra-rectal administration of 0.4 ml of a 25 mg/ml TNBS solution dissolved in 50% ethanol using an 8-cm long rubber catheter. Then, 0.4 ml of air was injected and the rats were kept in a Trendelenburg position for 30 sec to ensure that all TNBS solution left the catheter. Three rats received intra-rectal administration of saline and served as the negative control group. Coltect, 5-ASA, or their combination, were delivered by daily gavage of 0.5 ml solution starting from day 0.

All rats were sacrificed after 7 days. Their 10-cm distal colon was removed, opened longitudinally along the anti-mesenteric side and was gently washed with ice-cold saline in order to remove all luminal content. Colon wet weight was weighed and the colonic injury was immediately examined under a stereomicroscope and the visible damage was scored, then part of the colons was placed in 10% formalin for histological evaluation and parts were frozen at 800 C for later evaluation.

The induction and severity of colitis were evaluated by measuring:
1. Daily body weight.
2. Colon weight.
3. Macro-Histological score damage.

Figure 6:
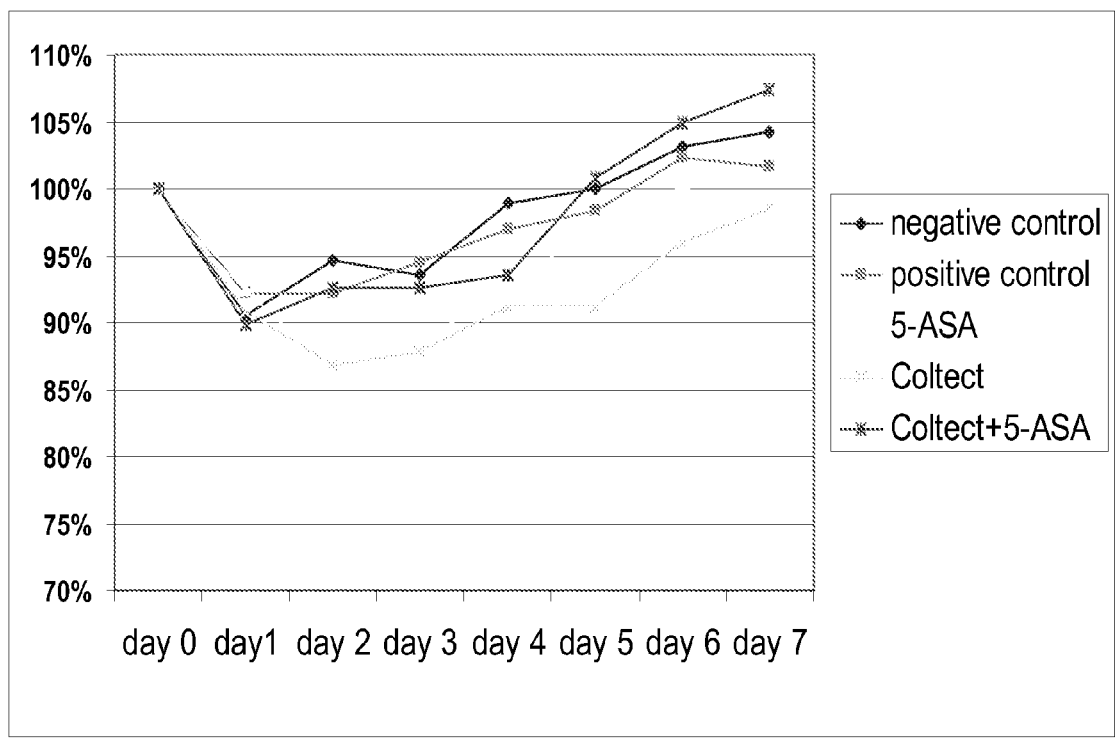
FIG. 6 is a graphical representation of changes in body weight of TNBS-induced model rats.

Reference is now made to FIG. 6 which relates to the weight-change in TNBS-induced model mice treated with the Coltect mixture, the 5-ASA drug or with their combination. As can be seen no substantial changes in body weight were observed during the experiment when treating the mice with Coltect, 5-ASA or their combination as compared to the negative and positive controls. Nevertheless, it is envisaged that an improvement in these results can be achieved without undue experimentation.

Figure 7:
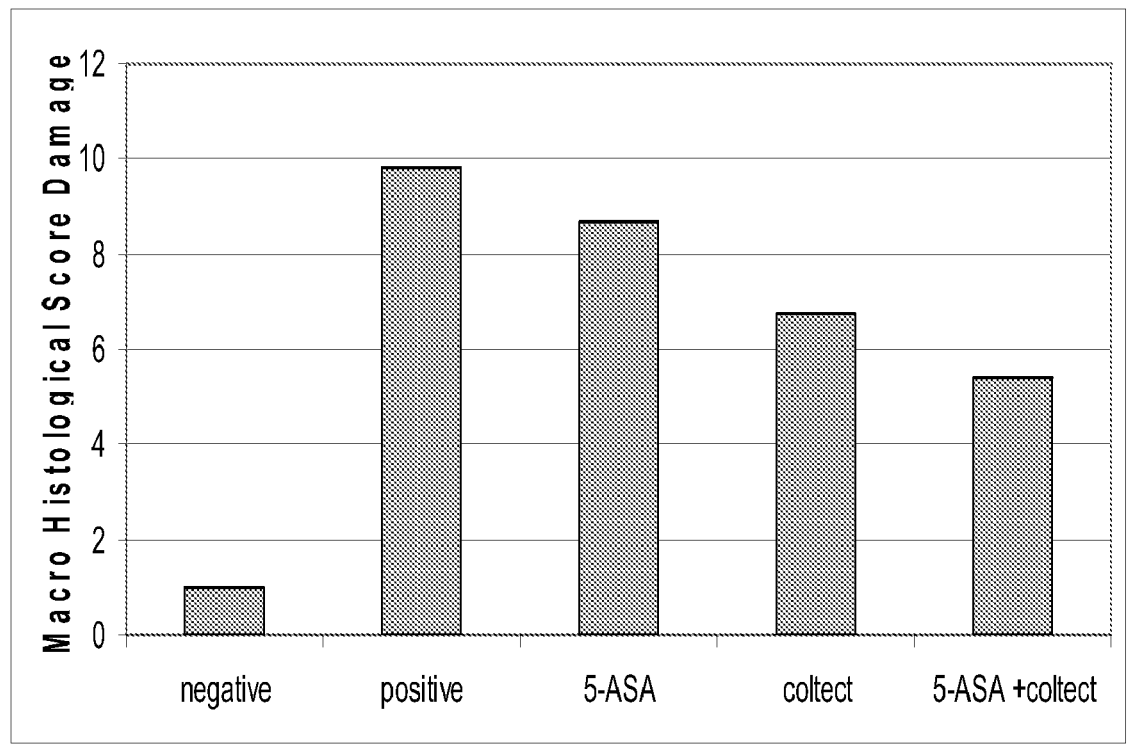
FIG. 7 is a graphical representation of Macro-histological score damage of TNBS-induced model rats.

Reference is now made to FIG. 7 showing the macro-histological score damage in TNBS-induced treated rates. As demonstrated, the macro-histological score damage was reduced by an average of about 40% in the aforesaid rates treated with the Coltect mixture of the present invention as compared to the positive control rates. Application of the 5-ASA drug, in combination with the Coltect mixture, exhibited an additive effect with respect to the reduction in macro-histological score damage, as compared to the positive control and to the effect conferred by each treatment separately.

Thus, the above experiments demonstrate the effectiveness of the Coltect mixture of the present invention in treating IBD and CRC. The improvement in IBD and CRC symptoms is significantly enhanced by administering the Coltect mixture in combination with the extensively used 5-ASA anti-inflammatory drug.

Example 4

Effect of Coltect In Vitro on the Growth of Colon Cancer HT-29 Cells

Figure 8:
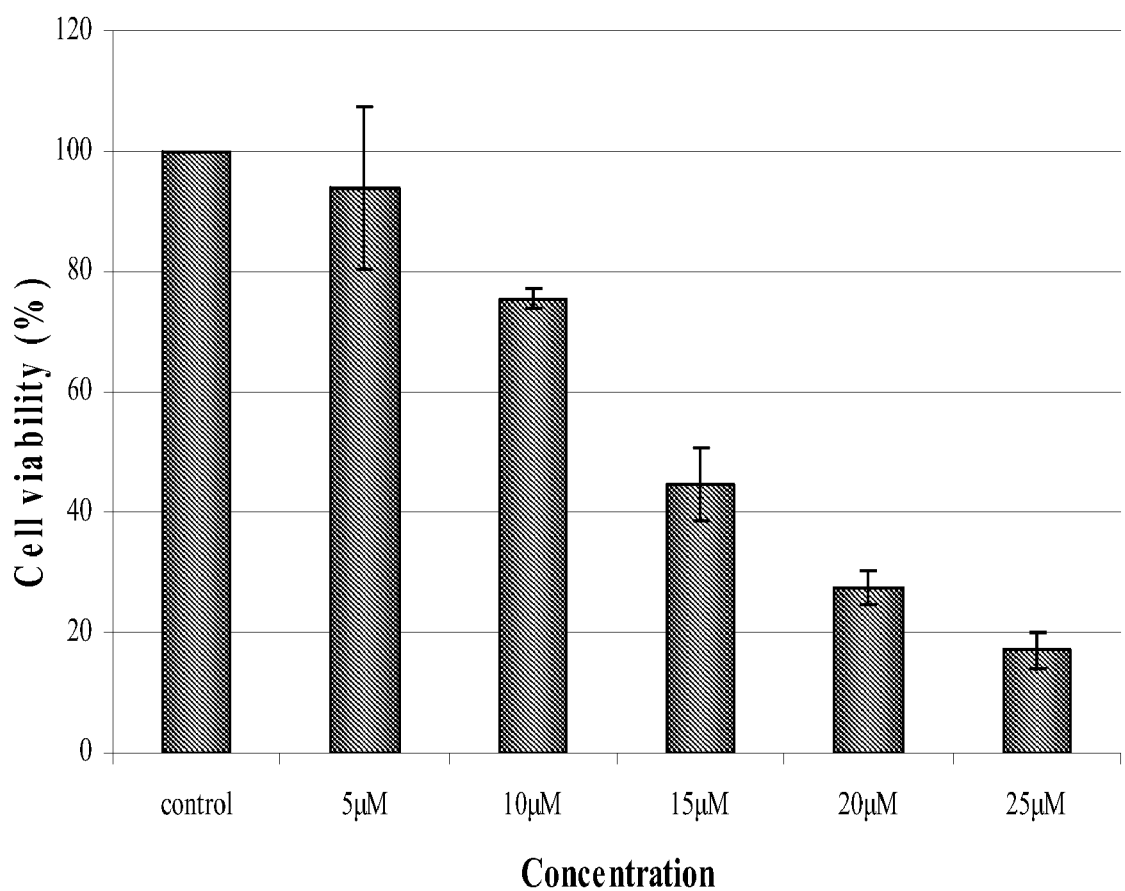
FIG. 8 is a graphical representation of growth inhibition assay of HT-29 colon cancer cells by the Coltect composition of the present invention.

The effect of Coltect was examined in vitro on HT-29 colon cancer cells by growth inhibition assay. HT-29 cells were exposed for 72 hours to various concentrations of Coltect, as indicated in FIG. 8. The data presented are mean±SD values from three independent experiments performed in duplicates. Cell growth after exposure to Coltect is compared to the untreated control cells. Differences in cell growth were determined by Students t test. Statistical significance: $p<0.05$.

The results show that HT-29 cells exhibit a dose dependent response to Coltect (FIG. 8). Thus these experiments demonstrate that the Coltect compound of the present invention inhibits the growth of HT-29 cells in a dose-dependent manner.

Example 5

Effect of Coltect as Compared to its Ingredients Administered Separately or in Partial Combination In order to assess the contribution of each of the Coltect components to its therapeutic effects in vivo, and to evaluate its additive therapeutic effect in comparison to each of its ingredients administered separately or in partial combination, a series of experiments were conducted in CRC and IBD model animals.

In these experiments the concentration of the ingredients used was determined based on their ratio in the Coltect mixture. As used in the above experiments, the Coltect concentration administered to the model animals was 150 mg/kg. Since a ratio of ⅔ Curcumin to ⅓ Green Tea was used in the Coltect mixture, the administered Curcumin concentration was 100 mg/kg and the Green tea concentration was 50 mg/kg. The Curcumin to Selenium ratio in the Coltect mixture was 500 mg Curcumin to 0.1 mg Selenium, therefore, the administered Selenium concentration was 0.02 mg/kg body weight. The final administered concentrations of the Coltect components are presented in Table 6 below:

TABLE 6

| Coltect- ingredient concentration | |
|---|---|
| Coltect ingredient | Ingredient concentration per 150 mg/kg Coltect mixture |
| Curcumin | 100 mg/kg |
| Green Tea | 50 mg/kg |
| Selenium | 0.02 mg/kg | a. Effect of Coltect and its Ingredients on DMH-Induced ACF Formation

Forty seven age- and sex-matched Wistar rats were obtained from the animal facility at TASMC. The rats were injected subcutaneously twice a week for two weeks with 0.3 ml of 50 mg/kg body weight DMH (Sigma-Aldrich, Israel) dissolved in PBS, and groups were randomly divided as shown in Table 7. The Coltect compound and its components were daily administered simultaneously for 2 weeks by oral gavage. The rats were sacrificed after 2 months.

TABLE 7

| DMH- induced treatment groups | | | |
|---|---|---|---|
| Group | No. of rats | DMH | Treatment |
| 1 (Negative control) | 5 | — | — |
| 2 (Positive control) | 7 | 50 mg/kg | — |
| 3 | 5 | 50 mg/kg | Cur |
| 4 | 5 | 50 mg/kg | GTE |
| 5 | 5 | 50 mg/kg | Se |
| 6 | 5 | 50 mg/kg | Cur + GTE |
| 7 | 5 | 50 mg/kg | Cur + Se |
| 8 | 5 | 50 mg/kg | GTE + Se |
| 9 | 5 | 50 mg/kg | Coltect 150 mg/kg |

Figure 9:
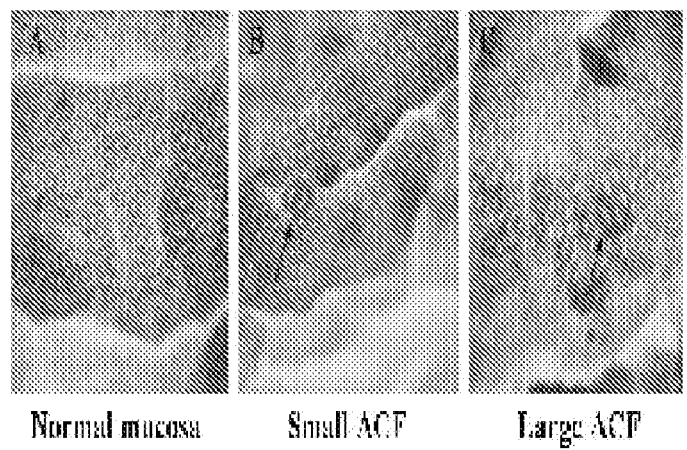
FIG. 9 is a photographic visualization of aberrant crypt foci (ACF) in DMH-induced rats.

Cur—Curcumin + curcum extract diluted 1:1
GTE—Green tea extract
Se—Selenomethionine Reference is now made to FIG. 9 presenting Methylene blue ACF staining performed according to the protocol described in the above Example 1, of normal mucosa (A) aberrant crypt foci containing small ACF with 1-3 crypts (B) and large ACF with more than three crypts (C).

Figure 10A:
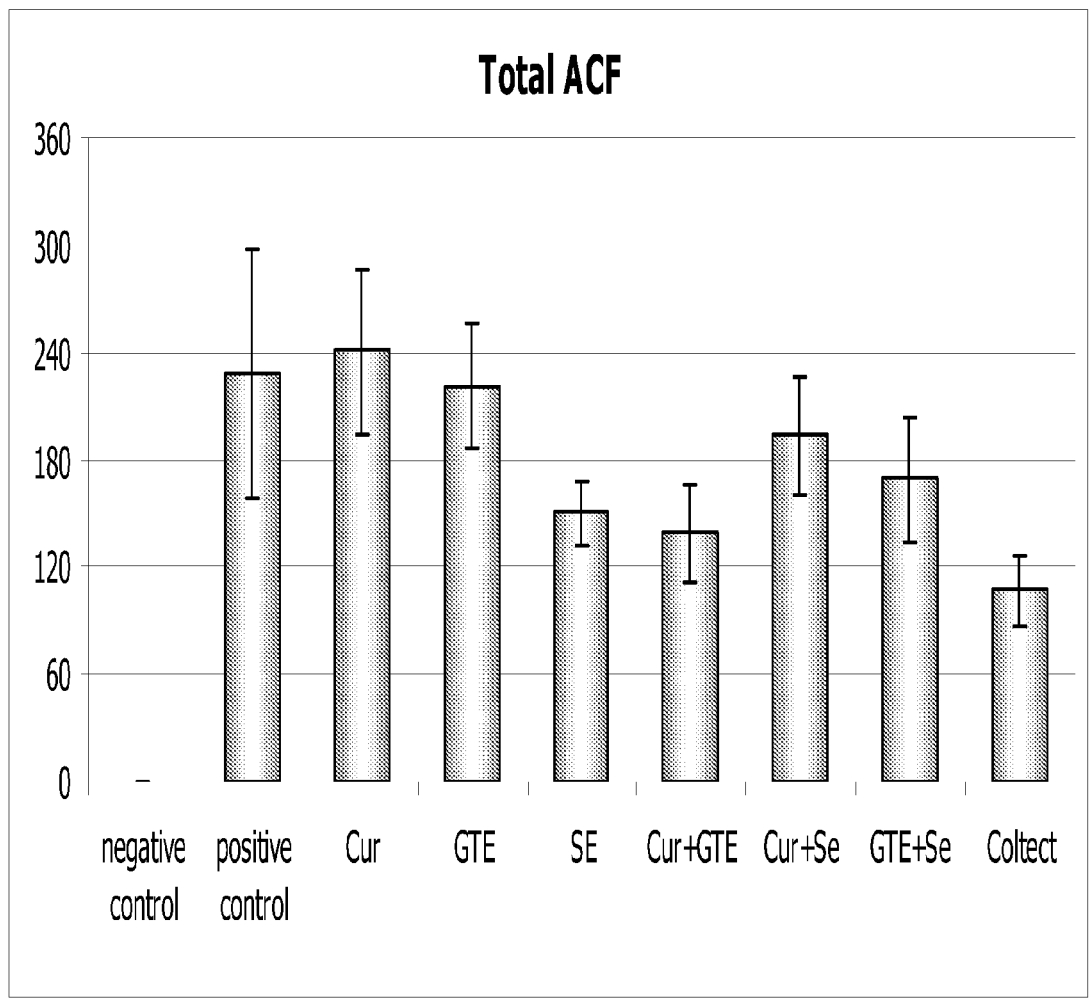
FIG. 10A is a graphical representation of total number of ACF in DMH-induced rats treated with Coltect, its components, separately or in combination.
Figure 10B:
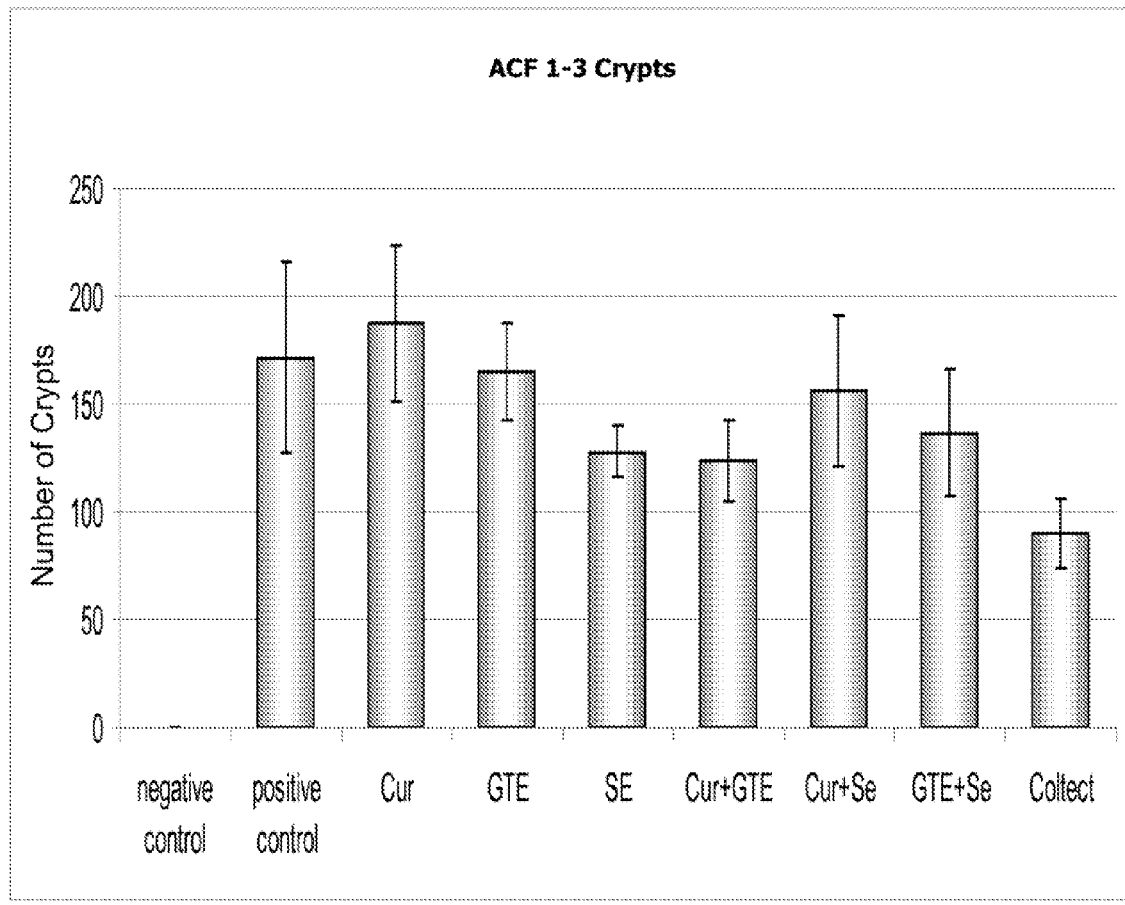
FIG. 10B is a graphical representation of the number of ACF comprising 1-3 crypts in DMH-induced rats treated with Coltect, its components, separately or in combination.
Figure 10C:
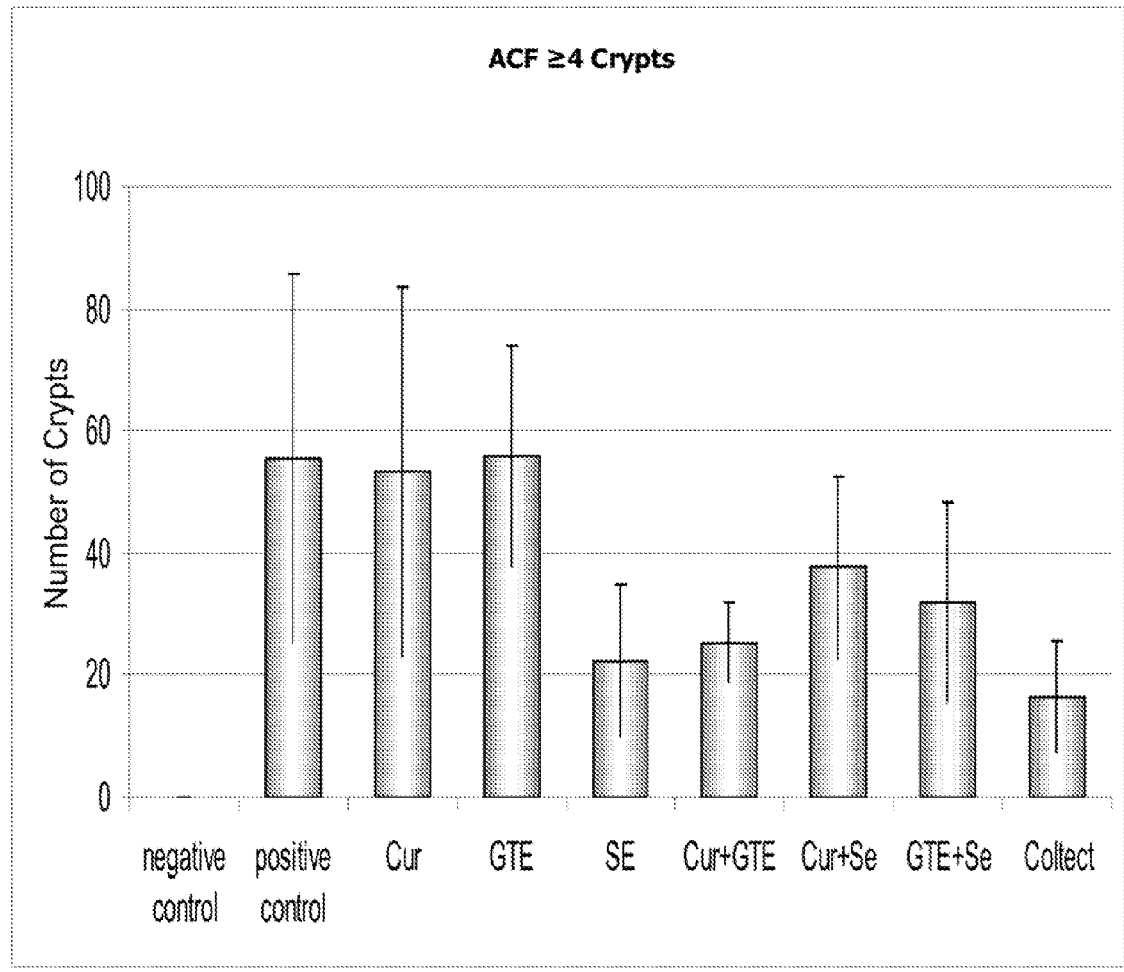
FIG. 10C is a graphical representation the number of ACF comprising more than three crypts in DMH-induced rats treated with Coltect, its components, separately or in combination.

Reference is now made to FIG. 10 presenting the effect of the Coltect composition on ACF formation as compared to each of its ingredients, separately and in partial combination. FIG. 10A relates to the total number of ACF in DMH-induced rats, whereas FIGS. 10B and 10C relates to the number of ACFs formed with average number of crypts lower than four (FIG. 10B) or higher than three (FIG. 10C). The results presented in FIG. 10A demonstrate that the Coltect mixture of the present invention has a significantly higher therapeutic effect on ACF formation relative to the effect of each of its components when said components are administered separately or in partial combination. By administering the Coltect mixture of the present invention to CRC model rats, the number of ACFs has been reduced by about 50% relative to the positive control, whereas no improvement in ACF formation was observed after administration of identical amounts of Curcumin or Green tea. Selenium administration merely reduced the number crypts by about 30%.

These results demonstrate that the specific and novel pharmaceutical composition of the present invention has a synergistic therapeutic effect on DMH-induced CRC model rats relatively to each of its ingredients administered separately or in partial combination. The synergistic therapeutic effect of the Coltect composition was further validated when the ACF tested contained average number of crypts lower than four (FIG. 10B) and when the ACF average number of crypts was higher than three (FIG. 10C).

b. Effect of Coltect and its Components on DSS-Induced Colitis in Mice

Age- and sex-matched C57BL 5-weeks old female mice were obtained from Harlan Laboratories, Israel. After one week of acclimation, the mice (n=52) were treated with 2.5% DSS administered in the drinking water for 5 days ad libitum, followed by two days of tap water. The treatments were given in doses of 0.3 ml of tap water with 2% DMSO by oral gavage. The mice were randomly divided into 8 sub-groups (n=6) and a control group (n=4) treated as described in Table 8.

TABLE 8

DSS- induced treatment groups

| Group | No. of mice | DSS (%) | Treatment |
|---|---|---|---|
| 1 (Negative control) | 4 | — | — |
| 2 (Positive control) | 6 | 2.5 | — |
| 3 | 6 | 2.5 | Coltect |
| 4 | 6 | 2.5 | Curcumin |
| 5 | 6 | 2.5 | Green tea |
| 6 | 6 | 2.5 | Selenium |
| 7 | 6 | 2.5 | Curcumin + Green tea |
| 8 | 6 | 2.5 | Green tea + selenium |
| 9 | 6 | 2.5 | Curcumin + Selenium |

Figure 11:
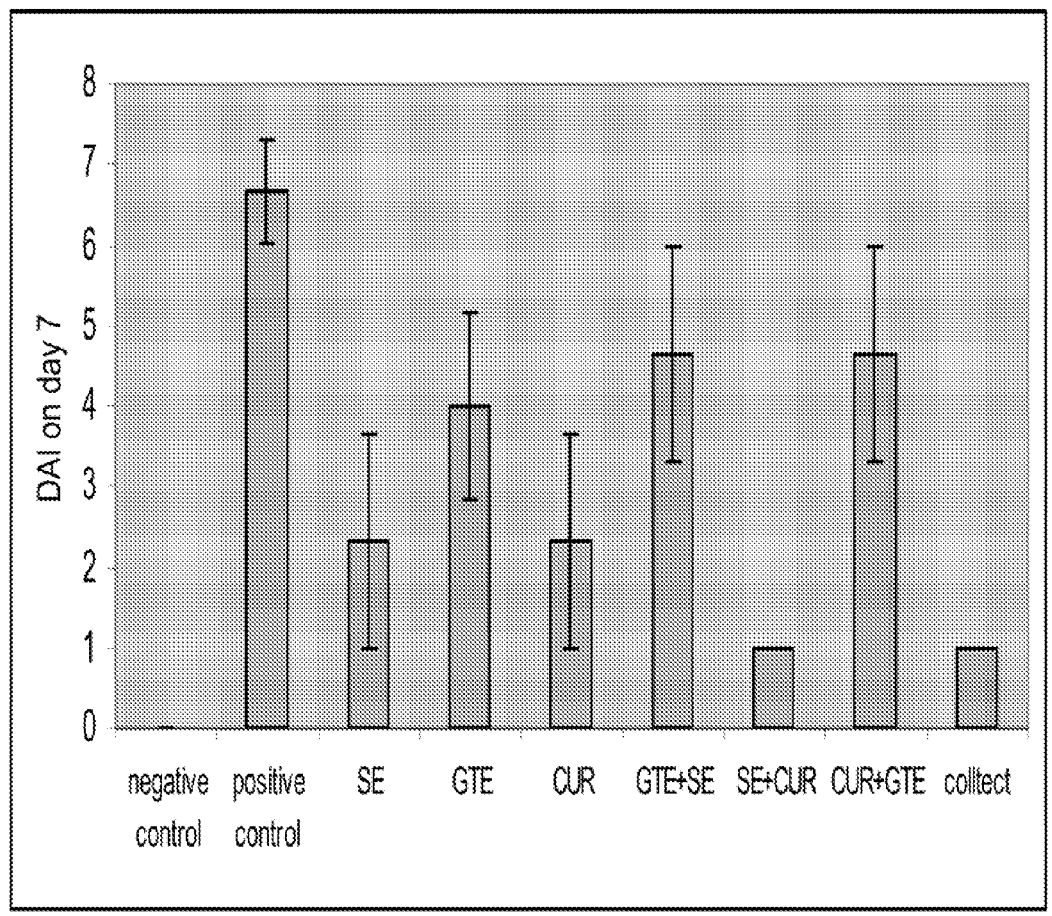
FIG. 11 is a graphical representation of DAI scores in DSS-induced mice treated with Coltect, its components, separately or in combination.

FIG. 11 shows the DAI score of mice subjected to DSS-induced colitis and treated with the Coltect composition or with curcumin, green tea, and selenium separately or in partial combination. The results show that mice treated with green tea, green tea and selenium and green tea with curcumin had the lowest improvement in disease symptoms and thus presented high DAI scoring of 4±1.15, 4.66±1.33 and 4.66±1.33, respectively. Mice treated with curcumin or with selenium alone showed a lower DAI scoring of 2.33±1.33. However, the mice treated with Coltect or with the combined treatment of selenium and curcumin exhibited the lowest DAI score as compared to the positive control (FIG. 11). Therefore these results indicate that the combination of selenium and curcumin significantly contribute to the therapeutic effect of Coltect in DSS-induced colitis model of mice.

These experiments provide further validation of the disclosure that the contribution of each ingredient to the Coltect therapeutic activity is not only additive but rather a synergistic effect. The combination of the specific Coltect components in their specific concentrations enables its effective biological activity in treatment of CRC and IBD.

Figure 12:
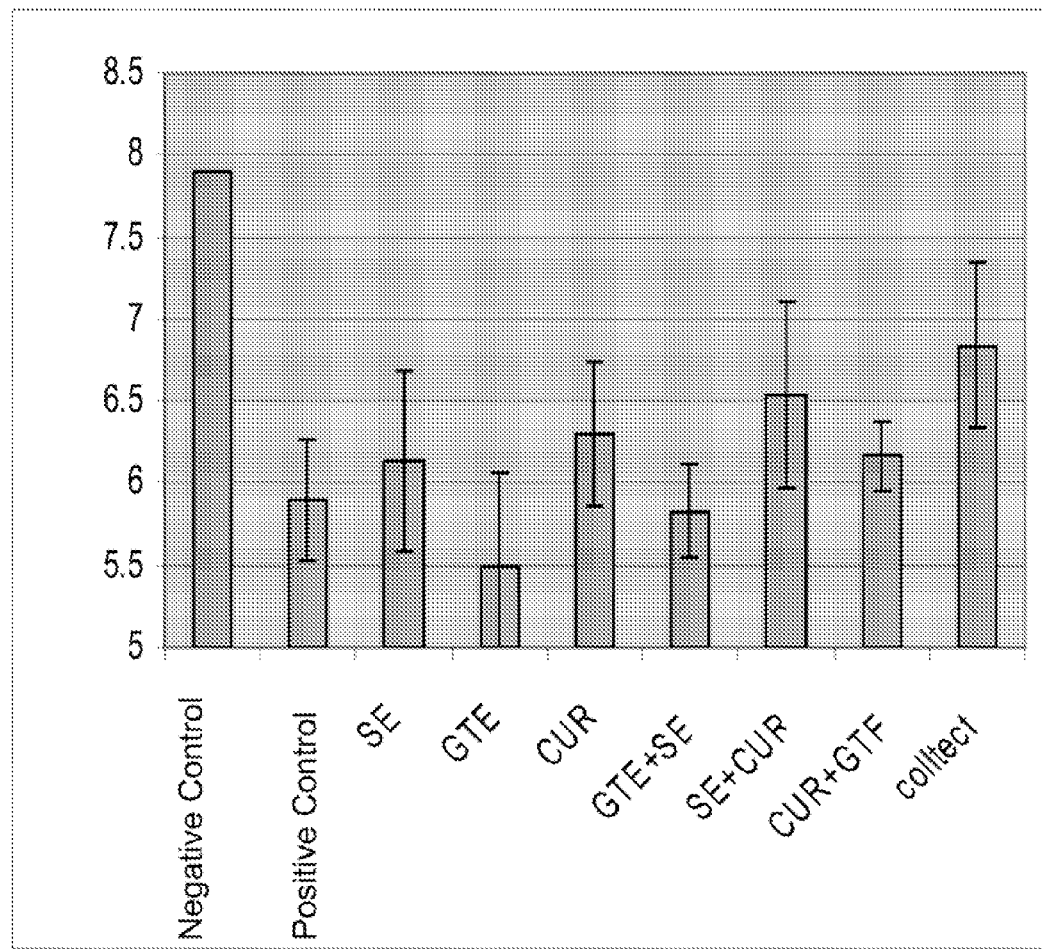
FIG. 12 is a graphical representation of changes in colon length in DSS-induced mice treated with Coltect, its components, separately or in combination.
Figure 13:
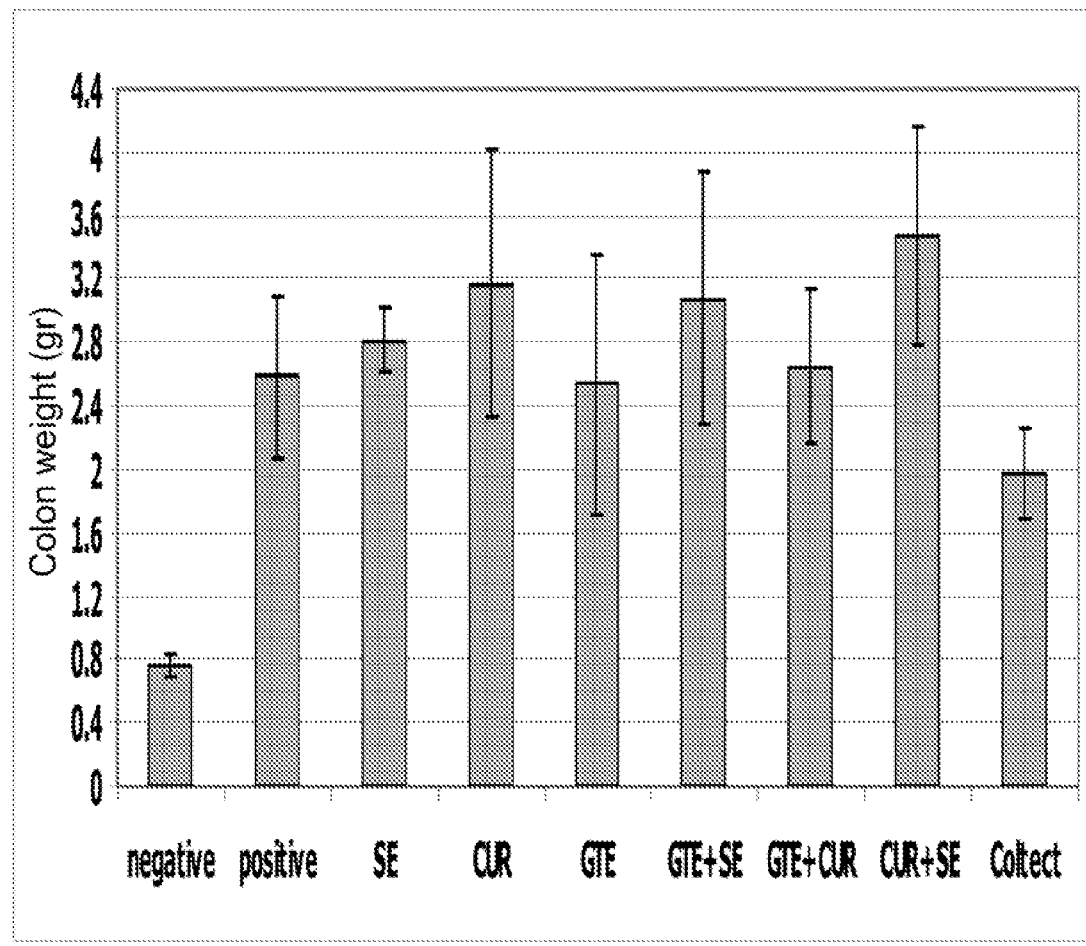
FIG. 13 is a graphical representation of colon weight in TNBS-induced rats treated with Coltect, its components, separately or in combination.
Figure 14:
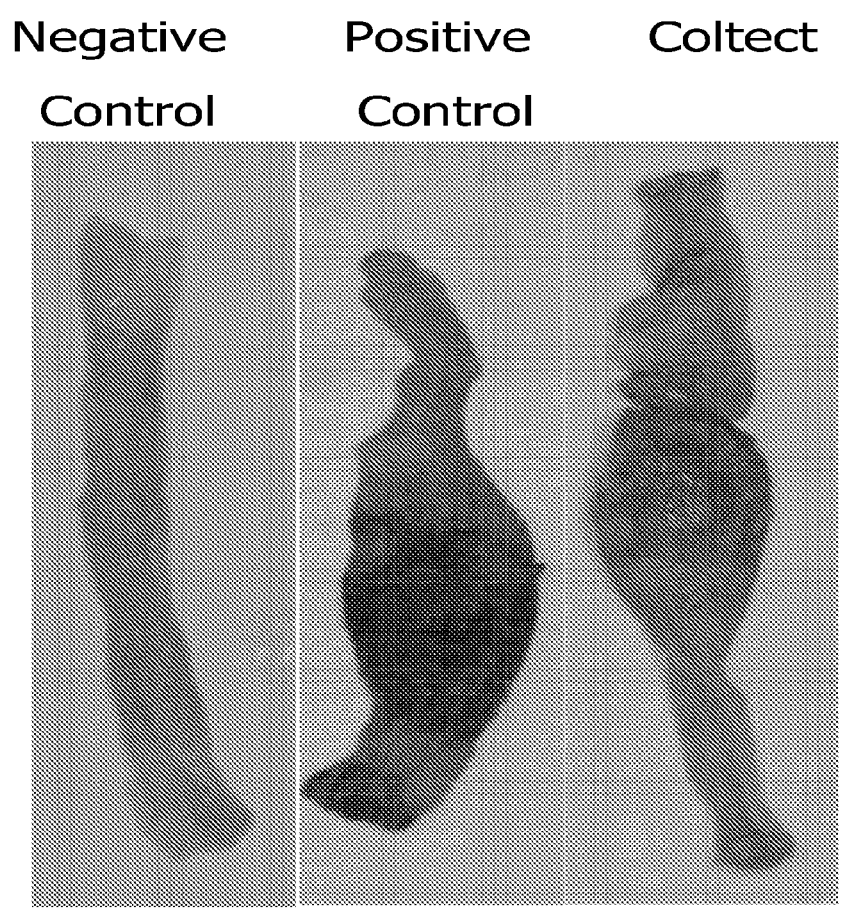
FIG. 14 is a photographic visualization of the effect of Coltect on colon length in TNBS-induced rats.
Figure 11:
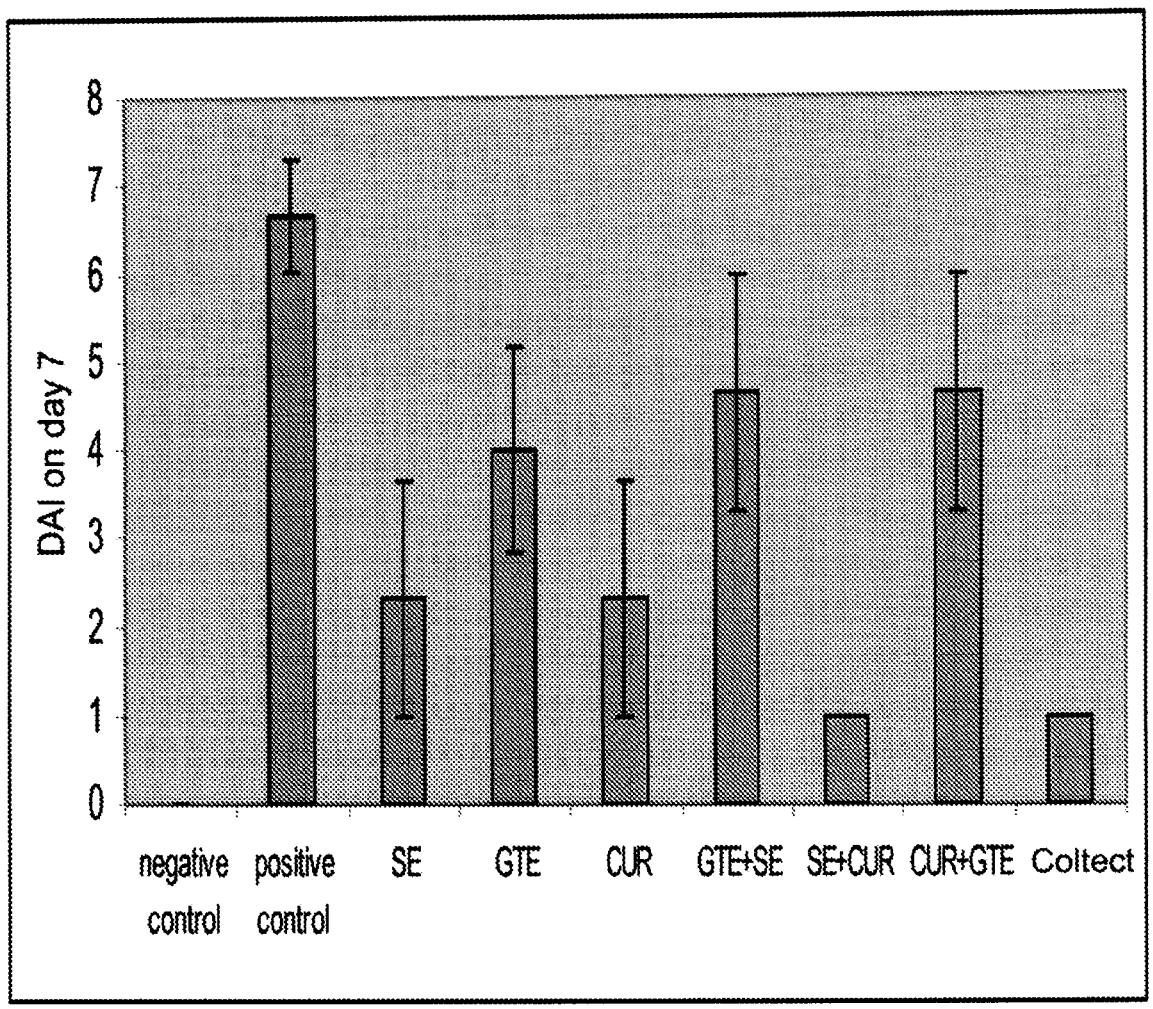
Figure 12:
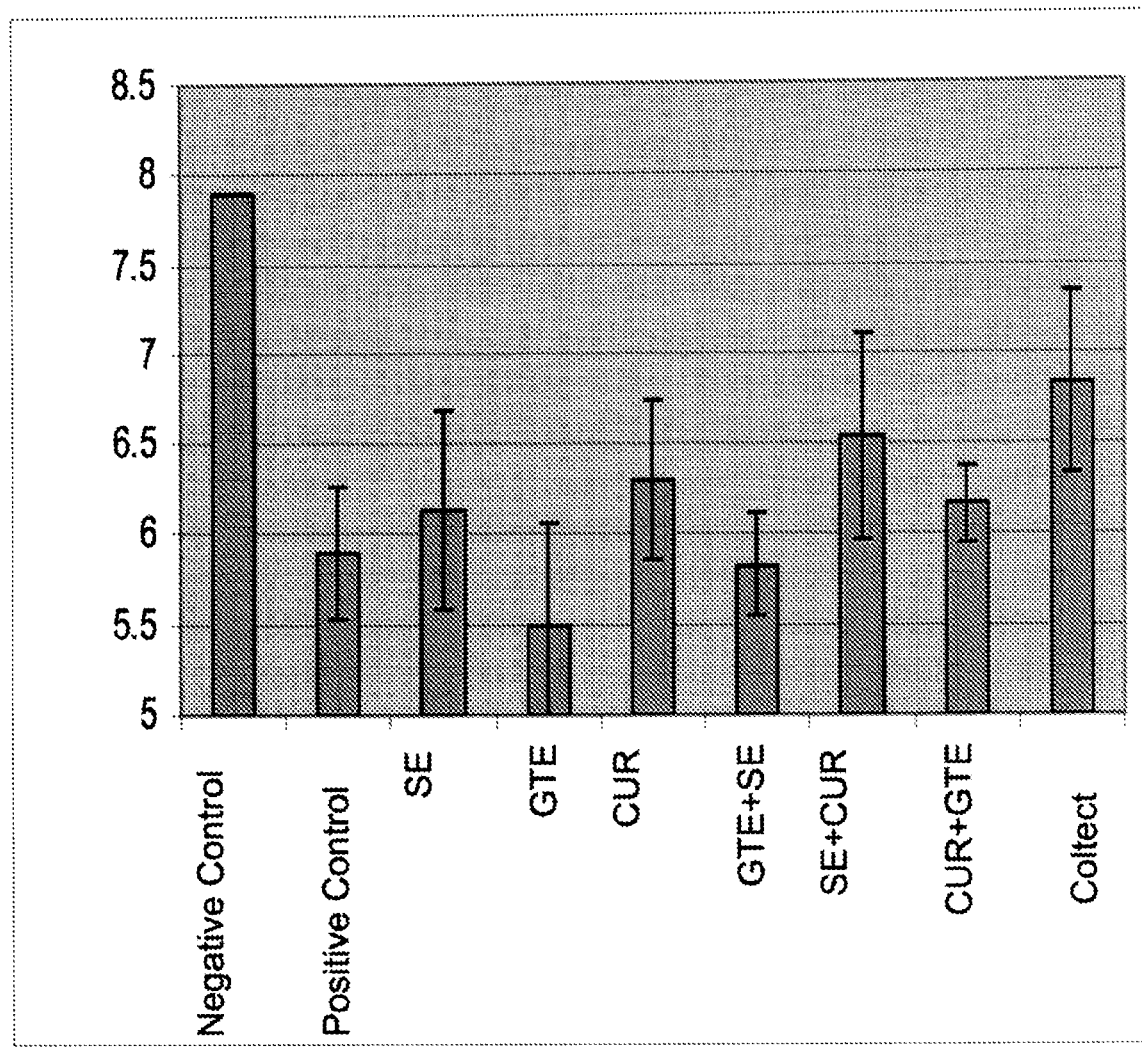

Reference is now made to FIG. 12 presenting differences in colon lengths in the DSS-induced mice. The colon lengths were measured from day seven of the experiment. The experiment was repeated twice. The data show that mice treated with green tea or green tea and selenium had colon lengths (5.5 and 5.8 cm, respectively) similar to the untreated positive control (5.8 cm). Thus these treatments are not effective in improving colitis symptoms in DSS-induced mice. The mice treated with selenium, curcumin or with a combination of both, had longer colons. Whereas mice treated with Coltect had the longest colons (6.8±0.29 cm) compared to all other treated mice. Thus these results demonstrate that the Coltect composition of the present invention synergistically improves colitis symptoms relative to is components administered separately or in partial combination.

c. Effect of Coltect and its Ingredients on TNBS-Induced Colitis Model in Rats:

The positive therapeutic effect of Coltect in colitis model rats is further demonstrated in FIG. 13, showing colon weight results obtained following colonoscopy. These results provide further validation for the synergistic activity of Coltect in treatment of colitis. Thus as shown in FIGS. 13 and 14, Coltect is more effective in reducing colon weight and preventing colon shortening than its separated components or their partial combination.

Example 6

Coltect Clinical Study

A phase 2A clinical study was conducted in 20 patients with mild-moderate ulcerative colitis with a clinical activity index (CAI) 4-8 as follows:
1. Two tablets of Coltect were administered twice daily for 8 weeks. Each tablet comprising, as detailed above, enterically coated Turmeric extract (95% curcuminoids), 250 mg; Turmeric powder, 250 mg; Green tea extract (60% polyphenols, 25% epigallocatechin gallate ECEG), 250 mg; Selenium (as Selenomethionine), 100 μg.
2. Sigmoidoscopy examination was performed at primary and end points of the study.
3. Stool testing, C-reactive protein (CRP) and blood count were performed at 0, 4 and 8 weeks of the study.
4. Improvement in CAI score and in sigmoidoscopy examination results was evaluated at the end of the study.

Study Progress:

More than 40 patients were screened, 22 patients enrolled and 21 patients completed the study.

Results

Patient distribution was as follows:
12 patients with improvement in disease symptoms
1 patient with exacerbation
2 patients with no improvement
6 patients dropped out of study Summary and Conclusions
1. Coltect inhibits the growth of CRC cells in vitro.
2. Coltect inhibits ACF formation in vivo, with similar efficacy to 5-ASA.
3. Coltect is effective in the treatment of mild-moderate ulcerative colitis.
4. Coltect synergistically improves CRC and IBD symptoms as compared to its separate components and their partial combination.
5. Coltect and 5-ASA synergistically prevent ACF formation.
6. This synergistic effect is clinically important as it can be used to treat inflammation and prevent cancer.

Reference is now made to a pharmaceutical composition consisting of natural ingredients, useful for treatment and prevention of medical disorders and ailments. The medical disorders and ailments are selected from a group consisting of inflammatory bowel disease (IBD) and colorectal cancer (CRC). The aforesaid composition comprising the following active ingredients: (a) a turmeric based first active ingredient comprising Turmeric extract, and Turmeric powder, and, (b) a second non turmeric based active ingredient, comprising a selenium element selected from a group consisting of Selenium or source of Selenium, especially Selenomethionine, and Green tea extract.

Reference is now made to the above defined pharmaceutical composition, wherein the pharmaceutical composition further comprises enteric coating encapsulating the same.

It is a core purpose of the invention that the pharmaceutical composition is especially adapted for treatment of inflammatory bowel disease (IBD) and colorectal cancer (CRC).

Reference is now made to the above defined pharmaceutical composition, wherein the Turmeric extract is provided in about 200 to about 300 mg and comprises about 95% curcuminoids; further wherein the Turmeric powder is provided in about 200 to about 300 mg.

Reference is now made to the above defined pharmaceutical composition, wherein the selenium element is provided in about 80 to about 120 µg of Selenium (elemental); and wherein the Green tea extract is optionally provided in about 200 to about 300 mg and comprises about 50% to about 70% polyphenols.

Reference is now made to the above defined pharmaceutical composition, wherein the composition is formulated in a tablet, caplet, capsule, lozenge, dragee or sachet form.

Reference is now made to the above defined pharmaceutical composition, wherein the enteric coating imparts protection to the composition so that the composition is protected in a low pH environment of about 3 or less while capable of releasing the composition at a pH of about 5.5 or higher.

Reference is now made to the above defined pharmaceutical composition, wherein the composition is encapsulated in the pharmaceutical composition coated by the enteric coating component Eudragit™.

Reference is now made to the above defined pharmaceutical composition, wherein the pharmaceutical composition additionally comprises 5-ASA (mesalamine) The pharmaceutical composition confers a synergistic therapeutic effect on subjects with respect to treatment of said IBD and/or CRC.

Reference is now made to the above defined pharmaceutical composition, wherein the pharmaceutical composition confers therapeutic effect on subjects with respect to development of IBD and/or CRC parameters compared to untreated controls. The parameters are selected from a group consisting of Disease Activity Index (DAI), induction and severity of colitis, macro-histological score damage, Aberrant Crypt Foci (ACF) formation, number of crypts and level of C-reactive protein (CRP).

Reference is now made to the above defined pharmaceutical composition, wherein the pharmaceutical composition provides a decrease in at least one of IBD or CRC parameters of at least 30%, the parameters selected from a group consisting of Disease Activity Index (DAI), induction and severity of colitis, macro-histological score damage, number of crypts and level of C-reactive protein (CRP) compared to untreated controls. The DAI score is further evaluated by parameters selected from a group consisting of weight loss, gross bleeding and stool consistency. The induction and severity of colitis is further evaluated by parameters selected from a group consisting of daily body weight, colon weight and macro-histological score damage.

Reference is now made to the above defined pharmaceutical composition, wherein the pharmaceutical composition further confers a synergistic therapeutic effect on subjects with respect to development of the IBD and/or CRC parameters compared to the therapeutic effect on said subject when said active ingredients of the pharmaceutical composition are administered to the subject separately and/or in partial combination.

Reference is now made to the above defined pharmaceutical composition, wherein the synergistic effect is at least 15% higher relative to the therapeutic effect on subjects with respect to development of the IBD and/or CRC parameters when active ingredients of the pharmaceutical composition are administered to the subject separately and or in partial combination.

Reference is now made to the above defined pharmaceutical composition, wherein the pharmaceutical composition provides a decrease in DAI score greater than the decrease provided by administering the active ingredients of the pharmaceutical composition to the subject separately or in partial combination.

Reference is now made to the above defined pharmaceutical composition, wherein the pharmaceutical composition provides a decrease in induction and severity of colitis greater than the decrease provided by administering the active ingredients of the pharmaceutical composition to the subject separately or in partial combination.

Reference is now made to the above defined pharmaceutical composition, wherein the pharmaceutical composition provides a decrease in number of Crypts and/or ACF formation greater than the decrease provided by administering the active ingredients of the pharmaceutical composition to the subject separately or in partial combination.

Reference is now made to the above defined pharmaceutical composition, wherein the pharmaceutical composition provides a decrease in the level of C-reactive protein (CRP) greater than the decrease provided by administering the active ingredients of the pharmaceutical composition to the subject separately or in partial combination.

Reference is now made to a method for treating and preventing medical disorders and ailments, selected from a group consisting of inflammatory bowel disease and colorectal cancer. The aforesaid method comprises steps of obtaining a pharmaceutical composition consisting of natural ingredients comprising the following active ingredients: (a) a turmeric based first active ingredient, comprising; Turmeric extract and Turmeric powder; and (b) a second non turmeric based active ingredient, comprising Green tea extract; and a Selenium element selected from a group consisting of Selenium, source of Selenium and Selenomethionine. The herein defined pharmaceutical composition is administered to a patient according to a predetermined protocol.

Reference is now made to the above defined method, wherein the method further comprises steps of providing the Turmeric extract in about 200 to about 300 mg. The turmeric extract comprises about 95% curcuminoids; further wherein the method further comprises steps of providing the Turmeric powder in about 200 to about 300 mg.

Reference is now made to the above defined method, wherein the method further comprises steps of providing the Green tea extract in about 200 to about 300 mg. The Green tea extract comprises about 50% to about 70% polyphenols. The method further comprises steps of providing the Selenium element with about 80 to about 120 µg Selenium.

Reference is now made to a method for treating and preventing medical disorders and ailments, especially inflammatory bowel disease and colorectal cancer. The aforesaid method comprises steps of obtaining the following ingredients: (i) Turmeric extract, containing about 200 to about 300 mg, about 95% curcuminoids; (ii) Turmeric powder, containing about 200 to about 300 mg; (iii) Green tea extract, containing about 200 to about 300 mg, about 50% to about 70% polyphenols and; (iv) Selenomethionine, containing about 80 to about 120 µg Selenium. The aforesaid method further comprises combining the ingredients into a pharmaceutical composition, coating the pharmaceutical composition with enteric coating encapsulating the same and, administering the pharmaceutical composition to a patient according to a predetermined protocol.

Reference is now made to the above defined method, wherein method further comprises steps of formulating said composition as a tablet, caplet, capsule, lozenge, dragee or sachet form.

Reference is now made to the above defined method, wherein the method further comprises steps of coating the pharmaceutical composition with enteric coating.

Reference is now made to the above defined method, wherein the method further comprises steps of providing protection to the composition so that the composition is protected in a low pH environment of about 3 or less while capable of releasing said composition at a pH of about 5.5 or higher.

Reference is now made to the above defined method, wherein the method further comprises steps of coating the pharmaceutical composition by enteric coating component, especially the enteric coating component Eudragit™.

Reference is now made to the above defined method wherein the method, additionally comprises steps of administering the pharmaceutical composition as a combined treatment with 5-ASA (Mesalamine).

Reference is now made to the above defined method, wherein the method additionally comprises steps of obtaining an effective measure of Mesalamine (5-ASA) before, whilst or after the step of abating the pharmaceutical composition.

Reference is now made to the above defined method, wherein the method additionally comprises steps of administering the pharmaceutical composition as a combined treatment with 5-ASA such that the treatment confers a synergistic therapeutic effect on subjects with respect to treatment of IBD and/or CRC.

Reference is now made to the above defined method, wherein the method further comprises steps of conferring therapeutic effect on subjects with respect to development of IBD and/or CRC parameters compared to untreated controls. The parameters are selected from a group consisting of DAI, induction and severity of colitis, macro-histological score damage, ACF formation, number of crypts, level of C-reactive protein (CRP).

Reference is now made to the above defined method, wherein the method further comprises steps of providing a decrease in at least one of IBD or CRC parameters of at least 30%, the parameters selected from a group consisting of DAI, induction and severity of colitis, macro-histological score damage, number of crypts and level of C-reactive protein (CRP) compared to untreated controls.

Reference is now made to the above defined method, wherein the method additionally comprises steps of combining the ingredients in predetermined amounts and proportions sufficient to confer a synergistic therapeutic effect on subjects with respect to development of IBD and/or CRC parameters and administering same.

Reference is now made to the above defined method, wherein the method additionally comprises steps of combining the active ingredients in predetermined amounts and proportions sufficient to confer a synergistic effect adapted to provide at least 15% increase relative to the therapeutic effect on subjects with respect to development of IBD and/or CRC parameters when active ingredients of the pharmaceutical composition are administered to the subject separately and or in partial combination.

Reference is now made to the above defined method, wherein the method additionally comprises steps of administering said pharmaceutical composition to said patient such that the decrease in DAI score is greater than the decrease provided by administering the active ingredients of the pharmaceutical composition to the subject separately or in partial combination.

Reference is now made to the above defined method, wherein the method additionally comprises steps of administering said pharmaceutical composition to said subject such that the decrease in induction and severity of colitis is greater than the decrease provided by administering the active ingredients of the pharmaceutical composition to the subject separately or in partial combination.

Reference is now made to the above defined method, wherein the method additionally comprises steps of administering said pharmaceutical composition to said subject such that the decrease in number of Crypts and/or ACF formation is greater than the decrease provided by administering the active ingredients of the pharmaceutical composition to the subject separately or in partial combination.

Reference is now made to the above defined method, wherein the method additionally comprises steps of administering said pharmaceutical composition to said subject such that the decrease in the level of C-reactive protein (CRP) is greater than the decrease provided by administering the active ingredients of the pharmaceutical composition to the subject separately or in partial combination.

Reference is now made to the above defined method, wherein the method is useful for treating Inflammatory Bowel Disease (IBD) and Colorectal Cancer (CRC).

The invention claimed is:

1. A pharmaceutical composition for treating inflammatory bowel disease consisting essentially of therapeutically effective amounts of turmeric extract, green tea extract and selenomethionine.

2. The pharmaceutical composition of claim 1, wherein said composition is in a form selected from the group consisting of tablet, caplet, capsule, lozenge, dragee and sachet.

3. The pharmaceutical composition of claim 1, wherein said composition contains about 200 to about 300 mg of turmeric extract and wherein said turmeric extract has about 95% curcuminoids.

4. The pharmaceutical composition of claim 1, wherein said composition contains about 200 to about 300 mg of green tea extract and wherein said green tea extract has about 50% to about 70% polyphenols.

5. An encapsulated pharmaceutical composition for treating inflammatory bowel disease consisting essentially of therapeutically effective amounts of turmeric extract, green tea extract, and selenomethionine, wherein said encapsulated pharmaceutical composition has an enteric coating which imparts protection to said composition so that said composition is protected in a low pH environment of about 3 or less while still being able to release said composition at a pH of about 5.5 or higher.

6. The pharmaceutical composition of claim 5, wherein said composition is encapsulated by an enteric coating of poly (meth)acrylate-based or methacrylic acid-methacrylic acid ester based component.

7. A pharmaceutical composition for treating inflammatory bowel disease consisting essentially of therapeutically effective amounts of turmeric extract, green tea extract, selenomethionine, and 5-aminosalicylic acid.

8. The pharmaceutical composition of claim 7, wherein said pharmaceutical composition confers a synergistic therapeutic effect on subjects with respect to treatment of said inflammatory bowel disease.

* * * * *

UNITED STATES PATENT AND TRADEMARK OFFICE
CERTIFICATE OF CORRECTION

PATENT NO. : 8,263,141 B2  
APPLICATION NO. : 12/789764  
DATED : September 11, 2012  
INVENTOR(S) : Daniel Katz Page 1 of 3

It is certified that error appears in the above-identified patent and that said Letters Patent is hereby corrected as shown below:

Delete Drawing Sheets 15 and 16 and substitute the attached sheets therefor showing Fig 11 and 12 correctly, with changes listed below.

| Fig. 11: | change "Colltect" | to | -- Coltect -- |
| Fig. 12: | change "CUR+GTF" | to | -- CUR+GTE -- |
| Fig. 12: | change "Colltect" | to | -- Coltect -- |

Replacement Drawing Sheets are provided herewith.

Signed and Sealed this  
Twelfth Day of February, 2013

Teresa Stanek Rea  
*Acting Director of the United States Patent and Trademark Office*